US011612612B2

(12) United States Patent
Malhotra et al.

(10) Patent No.: US 11,612,612 B2
(45) Date of Patent: Mar. 28, 2023

(54) PHARMACEUTICAL COMPOSITIONS

(71) Applicant: CIPLA LIMITED, Mumbai (IN)

(72) Inventors: Geena Malhotra, Mumbai (IN); Kalpana Joshi, Thane (IN); Jeevan Ghosalkar, Thane (IN); Preeti Raut, Mumbai (IN)

(73) Assignee: CIPLA LIMITED, Mumbai (IN)

(*) Notice: Subject to any disclaimer, the term of this patent is extended or adjusted under 35 U.S.C. 154(b) by 159 days.

(21) Appl. No.: 17/071,538

(22) Filed: Oct. 15, 2020

(65) Prior Publication Data

US 2021/0038619 A1 Feb. 11, 2021

Related U.S. Application Data

(62) Division of application No. 15/421,939, filed on Feb. 1, 2017, now abandoned.

(30) Foreign Application Priority Data

Feb. 12, 2016 (IN) .............................. 201621005051
Sep. 23, 2016 (IN) .............................. 201621032504
Nov. 30, 2016 (IN) .............................. 201621040945

(51) Int. Cl.
A61K 31/685 (2006.01)
A61K 45/06 (2006.01)
A61K 31/675 (2006.01)
A61K 31/34 (2006.01)
A61K 31/4525 (2006.01)
A61K 31/47 (2006.01)
A61K 31/506 (2006.01)
A61K 31/5365 (2006.01)
A61K 31/635 (2006.01)
A61K 9/24 (2006.01)
A61K 47/22 (2006.01)
A61K 9/20 (2006.01)
A61K 9/00 (2006.01)

(52) U.S. Cl.
CPC .......... A61K 31/685 (2013.01); A61K 9/0019 (2013.01); A61K 9/0053 (2013.01); A61K 9/20 (2013.01); A61K 9/209 (2013.01); A61K 9/2013 (2013.01); A61K 31/34 (2013.01); A61K 31/4525 (2013.01); A61K 31/47 (2013.01); A61K 31/506 (2013.01); A61K 31/5365 (2013.01); A61K 31/635 (2013.01); A61K 31/675 (2013.01); A61K 45/06 (2013.01); A61K 47/22 (2013.01)

(58) Field of Classification Search
CPC ...... A61K 45/06; A61K 31/47; A61K 31/506; A61K 31/675; A61K 47/22; A61P 31/12; A61P 31/18; A61P 31/20
See application file for complete search history.

(56) References Cited

U.S. PATENT DOCUMENTS

| 8,178,123 B2 | 5/2012 | Pauletti et al. |
| 11,234,981 B2* | 2/2022 | Malhotra ................. A61P 31/18 |
| 2021/0100786 A1* | 4/2021 | Malhotra ................. A61K 31/47 |
| 2022/0110938 A1* | 4/2022 | Malhotra ................. A61K 31/683 |

FOREIGN PATENT DOCUMENTS

| WO | 2003084462 A2 | 10/2003 |
| WO | 2004067018 A1 | 8/2004 |
| WO | 2015114340 A1 | 8/2015 |

OTHER PUBLICATIONS

"Piperine: Delightful surprise to the biological world, made by plant "pepper" and a great bioavailability enhancer for our drugs and supplements," World Journal of Pharmaceutical Research, vol. 3, Issue 6, 2084-2098.
"Immunotherapy," Wikipedia article, viewed online on Feb. 1, 2017 at https://en.wikipedia.org/wiki/Immunotherapy.
Chuchawankul, S., et al. "Piperine inhibits cytokine production by human peripheral blood mononuclear cells," Genetics and Molecular Research, 11 (1): 617-627, 2012.
"Piperine," Wikipedia article, viewed online on Feb. 1, 2017 at https://en.wikipedia.org/wiki/Piperine.
Tatiraju, Deepthi, V., et al. "Natural Bioenhancers: An Overview," Journal of Pharmacognosy and Phytochemistry, 2013; 2 (3): 55-60.
Abstract: Kasibhatta, R., et al. "Influence of piperine on the pharmacokinetics of nevirapine under fasting conditions: a randomised, crossover, placebo-controlled study," Drugs in R & D, 2007, 8 (6): 383-391.
Asif, Mohammed. "Oral Bioavailability Enhancement of an Anti-Viral Drug Using a Herbal Bio-Enhancer," dissertation submitted to the Faculty of Pharmacy, S.K. Patel College of Pharmaceutical Education and Research, Jul. 2009.
Prakash, Swati, et al. "Bioenhancement effect of piperine and ginger oleo resin on the bioavailability of atazanvir," International Journal of Pharmacy and Pharmaceutical Sciences, vol. 7, Issue 10, 2015.
Online forum discussion post, viewed online on Feb. 1, 2017 at http://forums.poz.com/index.php?topic=61045.0.
"Next Front in Worldwide AIDS Battle: Stretching Use of Anti-HIV Drugs" online Press Release dated Jul. 5, 2012, viewed online on Feb. 1, 2017 at http://www.hopkinsmedicine.org/news/media/releases/next_front_in_worldwide_aids_battle.
Patil, U.K., et al. "Role of Piperine As A Bioavailability Enhancer," 2016-2017 Citeweb.info, Abstract, viewed online on Feb. 1, 2017 at http://citeweb.info/20110699760.

(Continued)

Primary Examiner — My-Chau T. Tran
(74) Attorney, Agent, or Firm — Sorell, Lenna & Schmidt, LLP; William D. Schmidt

(57) ABSTRACT

An oral or injectable pharmaceutical composition is provided for treating diseases caused by retroviruses or hepatitis B viruses. The composition comprises a therapeutically effective amount of at least one anti-retroviral drug and a therapeutically effective amount of at least one pharmacokinetic booster or enhancer or derivative thereof. Methods and kits are also provided.

14 Claims, 8 Drawing Sheets

(56) References Cited

OTHER PUBLICATIONS

Dore et al., "Efficacy of Tenofovir Disoproxil Fumarate in Antiretroviral Therapy-Naive and-Experienced Patients Coinfected with HIV-1 and Hepatitis B Virus", 2004, The Journal of Infectious Diseases, 189(7), pp. 1185-1192. (Year: 2004).

Nunez et al., "Management of patients co-infected with hepatitis B virus and HIV", 2005, The Lancet Infec. Dis., 5(6), pp. 374-382. (Year: 2005).

Jiang et al., "Anti-HBV active constituents from Piper longum", 2013, Bioorganic & Medicinal Chemistry Letters, 23(7), pp. 2123-2127. (Year: 2013).

Haris et al., "Energetics, Thermodynamics, and Molecular Recognition of Piperine with DNA", 2015, J. Chem. Inf. Model., 55(12), pp. 2644-2656. (Year: 2015).

* cited by examiner

PHARMACEUTICAL COMPOSITIONS

CROSS REFERENCE TO RELATED APPLICATIONS

This application claims priority to Indian Provisional Patent Application Serial Number 201621005051, filed on Feb. 12, 2016, Indian Provisional Patent Application Serial Number 201621032504, filed on Sep. 23, 2016, and Indian Provisional Patent Application Serial Number 201621040945, filed on Nov. 30, 2016. These applications are incorporated herein by reference, in their entireties.

FIELD

The present invention relates to pharmaceutical compositions comprising at least one anti-retroviral drug and at least one pharmacokinetic booster or enhancer. The present invention also provides the manufacturing process thereof and use of the said compositions for the prevention, treatment or prophylaxis of diseases caused by viruses specifically caused by retroviruses or hepatitis B virus.

BACKGROUND

Human Immunodeficiency Virus (HIV), the virus that causes Acquired Immune Deficiency Syndrome (AIDS) has become one of the world's most serious health concern. HIV belongs to a class of viruses called retroviruses. Retroviruses are RNA (ribonucleic acid) viruses, and to replicate (duplicate), the viruses must make a DNA (deoxyribonucleic acid) copy of their RNA. It is the DNA genes that allow the virus to replicate. Like all viruses, HIV can replicate only inside cells, commandeering the cell's machinery to reproduce. Only HIV and other retroviruses, however, once inside a cell, use an enzyme called reverse transcriptase to convert their RNA into DNA, which can be incorporated into the host cell's genes.

HIV destroys $CD_4$ positive ($CD_4$) T cells, which are white blood cells crucial to maintaining the function of the human immune system. The destruction of these cells leaves people infected with HIV vulnerable to other infections, diseases and other complications. These cells, sometimes called "T-helper cells," play a central role in the immune response, signalling other cells in the immune system to perform their special functions. As HIV attacks these cells, the person infected with the virus is less equipped to fight off infection and disease, ultimately resulting in the development of AIDS.

A healthy, uninfected person usually has 800 to 1,200 $CD_4$ T cells per cubic millimeter ($mm^3$) of blood. HIV appears to have a particular affinity for the human T-4 lymphocyte cell which plays a vital role in the body's immune system. HIV infected white blood cells (WBCs) lead to a decrease in WBC population. Eventually, the immune system is rendered inoperative and ineffective against various opportunistic diseases. During untreated HIV infection, the number of these cells in a person's blood progressively declines. When the $CD_4$ T cell count falls below $200/mm^3$, a person becomes particularly vulnerable to the opportunistic infections and cancers that typify AIDS, the end stage of HIV disease. People with AIDS often suffer infections of the lungs, intestinal tract, brain, eyes, and other organs, as well as debilitating weight loss, diarrhea, neurologic conditions, and cancers such as Kaposi's sarcoma and certain types of lymphomas.

The first case was reported in 1981 and today there are approximately 36.9 million people currently living with HIV and tens of millions of people have died of AIDS-related causes since the beginning of the epidemic. While new cases have been reported in all regions of the world, approximately 70% are in sub-Saharan Africa. Further, as per the 2016 fact sheet of UNAIDS, in 2015, there were 36.7 million people living with HIV. As of December 2015, 17 million people living with HIV were accessing antiretroviral therapy. In 2015, 1.1 million people died from AIDS-related causes worldwide.

HIV is the causative agent of AIDS that has created a major health care problem not only in India but globally. AIDS causes a gradual breakdown of the body's immune system as well as progressive deterioration of the central and peripheral nervous systems. Since its initial recognition in the early 1980s, AIDS has spread rapidly and has now reached epidemic proportions within a relatively limited segment of the population. Intensive research has led to the discovery of the responsible agent, human T-lymphotropic retrovirus 111 (HTLV-111) commonly referred to as the Human Immunodeficiency Virus or HIV.

Currently available antiretroviral drugs for the treatment of HIV include: zidovudine or AZT (Retrovir®), didanosine or DDI (Videx®), stavudine or D4T (Zenith®), lamivudine or 3TC (Epivir®), zalcitabine or DDC (Hivid®), abacavir sulphate (Ziagen®), tenofovir disoproxil fumarate (Viread®), emtricitabine (Emtriva®), Combivir® (contains 3TC and AZT), Trizivir® (contains abacavir, 3TC and AZT), Epzicom® (contains abacavir and lamivudine); nevirapine (Viramune®), delavirdine (Rescriptor®), efavirenz (Sustiva®), saquinavir (Invirase®, Fortovase®), indinavir (Crixivan®), ritonavir (Norvir®), nelfinavir (Viracept®), amprenavir (Agenerase®), atazanavir (Reyataz®), Evotaz® (contains atazanavir and cobicistat), fosamprenavir (Lexiva®), Kaletra® (contains lopinavir and ritonavir), enfuvirtide (T-20, Fuzeon®), Truvada® (contains Tenofovir and Emtricitabine), darunavir (Prezista®), Prezcobix® (contains darunavir and cobicistat), dolutegravir (Tivicay®), Triumeq® (contains dolutegravir, abacavir and lamivudine), elvitegravir (Vitekta®), Genvoya® (contains elvitegravir, cobicistat, tenofovir alafenamide fumarte and emtricitabine), Stribild® (contains elvitegravir, cobicistat, tenofovir disoproxil fumarte and emtricitabine) raltegravir (Isentress®), Complera® (contains emtricitabine, tenofovir disoproxil fumarte, rilpivirine) and Atripla® (contains fixed-dose triple combination of tenofovir, emtricitabine and efavirenz).

Between 5 and 10% of people with HIV are also infected with hepatitis B virus (often called co-infection). People with HIV are less likely to naturally clear hepatitis B without treatment. People with HIV and hepatitis co-infection can have faster liver disease progression and may not respond as well to hepatitis B treatment. However, having hepatitis B does not seem to make HIV disease worse. Hepatitis B virus (HBV) infection is the most common chronic viral infection in the world. An estimated 2 billion people have been infected, and more than 350 million are chronic carriers of the virus. HBV is transmitted through contact with infected blood or semen.

Further, AIDS (HIV) and hepatitis B viruses are remarkably similar in their sharing of reverse transcription, in their ancestral origins and common genetic elements, and in their modes of transmission. Both are hypermutable and exist as quasi-species due primarily to errors in reverse transcription, though there is severe restriction in the replicative competence of most hepatitis B mutants. They differ in the lack of an integrase in hepatitis B virus and in their pathogenesis in the infected host. HIV survives mainly by antigenic variability, immune evasion, and impairment of immune function though viral regulatory control elements seeking to restrict fatal damage to the host. Hepatitis B virus survives primarily by mutation of e antigen/core genes that directly obviate cytotoxic T cell destruction of infected liver cells, or indirectly limit destruction of infected cells through induction of anergy in the cytotoxic T cell response.

Further, antiretroviral drugs such as lamivudine, adefovir, entecavir and tenofovir have been approved for the treatment of chronic HBV infection.

Pharmacokinetic boosters or enhancers are used to boost the effectiveness of antiretroviral drugs. When a pharmacokinetic booster or enhancer is co-administered with an antiretroviral drug, the pharmacokinetic enhancer interferes with the breakdown of the antiretroviral drug, which causes the antiretroviral drug to remain in the body for a longer time and at a higher concentration. Pharmacokinetic boosters or enhancers specifically cause inhibition of the cytochrome P450 3A4 enzyme system leading to an increase in the plasma concentrations of the co-administered antiretroviral drugs. Protease Inhibitors are one such class of antiretroviral drugs that generally exhibit high genetic barrier for drug resistance and hence do require a pharmacokinetic booster or enhancer to be co-administered. Out of all the approved drugs for the treatment of HIV, Ritonavir and Cobicistat are termed as pharmacokinetic "boosters" or "enhancers". Ritonavir is used because of its capacity to inhibit the drug metabolizing enzyme cytochrome P450 (CYP) 3A4. Given in a low dose, ritonavir reduces the metabolism of protease inhibitors such as lopinavir and atazanavir, which are extensively metabolized by CYP3A4, thus enhancing the drug exposure. Cobicistat is also a strong inhibitor of CYP3A isozymes and increases plasma concentrations of drugs which are metabolized by CYP3A such as protease inhibitors viz, atazanavir and darunavir.

Besides ritonavir and cobicistat, there are many naturally occurring substances which are reported in literature and may be explored to improve the pharmacokinetic activity of certain drugs.

These naturally occurring substances which act as bioenhancers are chemical entities that promote and augment the bioavailability of the drugs which are mixed with them and do not exhibit synergistic effect with the drug. Examples of these bioenhancers include piperine, garlic, *Carum carni*, *Cuminum cyminum*, lysergol, naringin, quercetin, niaziridin, glycyrrhizin, stevia, cow urine, distillate ginger, etc.

These pharmacokinetic "boosters" or "enhancers" might reduce the cost of antiviral therapy, reduce pill burden for patients, and/or reduce the risk of sub therapeutic antiviral concentrations (e.g., development of resistance as well as enhance adherence to antiviral therapy).

However, this pharmacokinetic enhancement can be associated with its own risks. The precipitant drug, e.g., the booster or enhancer may have to be administered in a dose that inhibits the elimination of the object drug as well as does not produce its own side effects.

Accordingly, the enhancer which usually is a potent inhibitor may unintentionally inhibit the elimination of other drugs, leading to unwanted adverse effects. Also, if the dose of the enhancer is not carefully adjusted, or is inadequate or in excess, it may ultimately cause either a decrease or an increase of the object drug concentration. Hence considering these aspects, selection of the appropriate dose of the enhancer plays a vital role.

For example, although ritonavir has antiviral activity, it causes undesirable side effects, including gastrointestinal problems especially chronic diarrhea and lipid abnormalities. Cobicistat was then developed to produce approximately the same degree of effect as ritonavir, but without antiviral activity or any other problematic side effects.

Cobicistat is a substrate for CYP3A4 (CYP2D6 is a minor pathway of metabolism) and inhibits its own metabolism. Further, cobicistat also inhibits P-glycoprotein (P-gp) and CYP2D6 and hence there are a number of potential interactions that may occur with cobicistat.

Further, patients that are being treated for HIV are always at risk for interactions with other non-HIV medication and cobicistat is known to exhibit key drug interactions with antacids, benzodiazepams, beta-blockers, calcium channel blockers, erectile dysfunction drugs, inhaled/injectable corticosteroids, statins, oral contraceptive progestins, rifampin and maraviroc.

The pharmacokinetic enhancers or boosters that are currently in use unintentionally inhibit the elimination of other drugs, leading to unwanted adverse effects. Also, the use of piperine and/or its structural analogs such as tetrahydropiperine, cis, trans-piperine, trans, cis-piperine, cis,cis-piperine and trans,trans-piperine are not known to enhance the bioavailability of such anti-retroviral drugs.

Therefore, there remains a need to provide a combination therapy of a pharmacokinetic booster or enhancer with such anti-retroviral drugs for the treatment of HIV which reduces the dose of such anti-retroviral drugs, side effects exhibited by these drugs as well as maintains the optimal concentration of the same. Further, use of a naturally occurring pharmacokinetic booster or enhancer would eliminate or reduce interactions with other non-HIV medications that would be concurrently administered.

SUMMARY

In some embodiments, an object of the present invention is to provide a composition comprising at least one anti-retroviral drug and at least one pharmacokinetic booster or enhancer.

In some embodiments, another object of the present invention is to provide a composition comprising at least one anti-retroviral drug and at least one pharmacokinetic booster or enhancer with reduced side effects.

In some embodiments, yet another object of the present invention is to provide a composition comprising at least one anti-retroviral drug and at least one pharmacokinetic booster or enhancer with reduced drug interactions.

In some embodiments, another object of the present invention is to provide a composition comprising at least one anti-retroviral drug and at least one pharmacokinetic booster or enhancer for once or twice a day administration.

In some embodiments, another object of the present invention is to provide a composition comprising at least one anti-retroviral drug and at least one pharmacokinetic booster or enhancer with a reduced dose.

In some embodiments, yet another object of the present invention is to provide a composition comprising at least one anti-retroviral drug and at least one pharmacokinetic booster or enhancer in the form of a kit.

In some embodiments, yet another object of the present invention is to provide a method of prevention, treatment or prophylaxis of diseases caused by viruses specifically caused by retroviruses, specifically Acquired Immune Deficiency Syndrome or an HIV infection, the method comprising administering at least one anti-retroviral drug and at least one pharmacokinetic booster or enhancer.

In some embodiments, yet another object of the present invention is to provide a method of treatment of diseases caused by viruses specifically caused by hepatitis B virus, the method comprising administering at least one anti-retroviral drug and at least one pharmacokinetic booster or enhancer.

In some embodiments, yet another object of the present invention is to provide use of a pharmaceutical composition comprising at least one anti-retroviral drug and at least one pharmacokinetic booster or enhancer for the treatment or prophylaxis of diseases caused by viruses specifically caused by retroviruses, specifically Acquired Immune Deficiency Syndrome or an HIV infection.

In some embodiments, yet another object of the present invention is to provide the use of a pharmaceutical composition comprising at least one anti-retroviral drug and at least one pharmacokinetic booster or enhancer for the treatment of diseases caused by viruses specifically hepatitis B virus.

According to an aspect of the present invention, provided is a pharmaceutical composition comprising at least one anti-retroviral drug and at least one pharmacokinetic booster or enhancer and one or more pharmaceutically acceptable excipient.

According to another aspect of the invention, provided is a process for preparing a pharmaceutical composition comprising at least one anti-retroviral drug and at least one pharmacokinetic booster or enhancer with at least one or more pharmaceutically acceptable excipients.

According to another aspect of the present invention, provided is a method of treating diseases caused by viruses specifically caused by retroviruses, especially AIDS or an HIV infection, the method comprising administering a therapeutically effective amount of a pharmaceutical composition comprising at least one anti-retroviral drug and at least one pharmacokinetic booster or enhancer according to the present invention to a patient in need thereof.

According to another aspect of the present invention there is provided a method of treating diseases caused by viruses specifically caused by hepatitis B virus, the method comprising administering a therapeutically effective amount of a pharmaceutical composition comprising at least one anti-retroviral drug and at least one pharmacokinetic booster or enhancer according to the present invention to a patient in need thereof.

According to another aspect of the present invention provided is the use of a pharmaceutical composition comprising at least one anti-retroviral drug and at least one pharmacokinetic booster or enhancer according to the present invention in the manufacture of a medicament for the treatment of diseases caused by viruses, specifically caused by retroviruses, especially AIDS or an HIV infection.

According to another aspect of the present invention there is provided the use of a pharmaceutical composition comprising at least one anti-retroviral drug and at least one pharmacokinetic booster or enhancer according to the present invention in the manufacture of a medicament for the treatment of diseases caused by viruses, specifically caused by hepatitis B virus.

In some embodiments, an oral or injectable pharmaceutical composition is provided comprising a therapeutically effective amount of at least one anti-retroviral drug and a therapeutically effective amount of at least one pharmacokinetic booster or enhancer or derivative thereof.

In some embodiments, an oral or injectable pharmaceutical composition is provided comprising a therapeutically effective amount of at least one anti-retroviral drug; a therapeutically effective amount of at least one pharmacokinetic booster or enhancer or derivative thereof; and one or more pharmaceutically acceptable excipients comprising carriers, diluents, fillers, binders, lubricants, glidants, disintegrants, bulking agents, flavorants or any combination thereof.

In some embodiments, a method of treating diseases caused by retroviruses or hepatitis B viruses in a patient in need of such treatment is provided, the method comprising: administering a pharmaceutical composition comprising (i) a therapeutically effective amount of at least one anti-retroviral drug or an antiviral drug; (ii) a therapeutically effective amount of at least one pharmacokinetic booster or enhancer or derivative thereof; and (iii) one or more pharmaceutically acceptable excipients comprising carriers, diluents, fillers, binders, lubricants, glidants, disintegrants, bulking agents, flavourants or any combination thereof.

In some embodiments, a method of making a pharmaceutical composition that enhances the bioavailability of an anti-retroviral drug is provided, the method comprising: mixing a therapeutically effective amount of at least one anti-retroviral drug and a therapeutically effective amount of at least one pharmacokinetic booster or enhancer or derivative thereof with one or more pharmaceutically acceptable excipients to make the pharmaceutical composition.

In some embodiments, a kit for treating disease caused by retroviruses or hepatitis B viruses is provided, the kit comprising a therapeutically effective amount of at least one anti-retroviral drug and a therapeutically effective amount of at least one pharmacokinetic booster or enhancer or derivative thereof, wherein the at least one anti-retroviral drug is in a separate composition from the at least one pharmacokinetic booster or enhancer or derivative thereof.

In some embodiments, a method of enhancing the bioavailability of an oral anti-retroviral drug is provided, the method comprising: providing a therapeutically effective amount of at least one anti-retroviral drug and providing a therapeutically effective amount of at least one pharmacokinetic booster or enhancer or derivative thereof.

Figure 1:
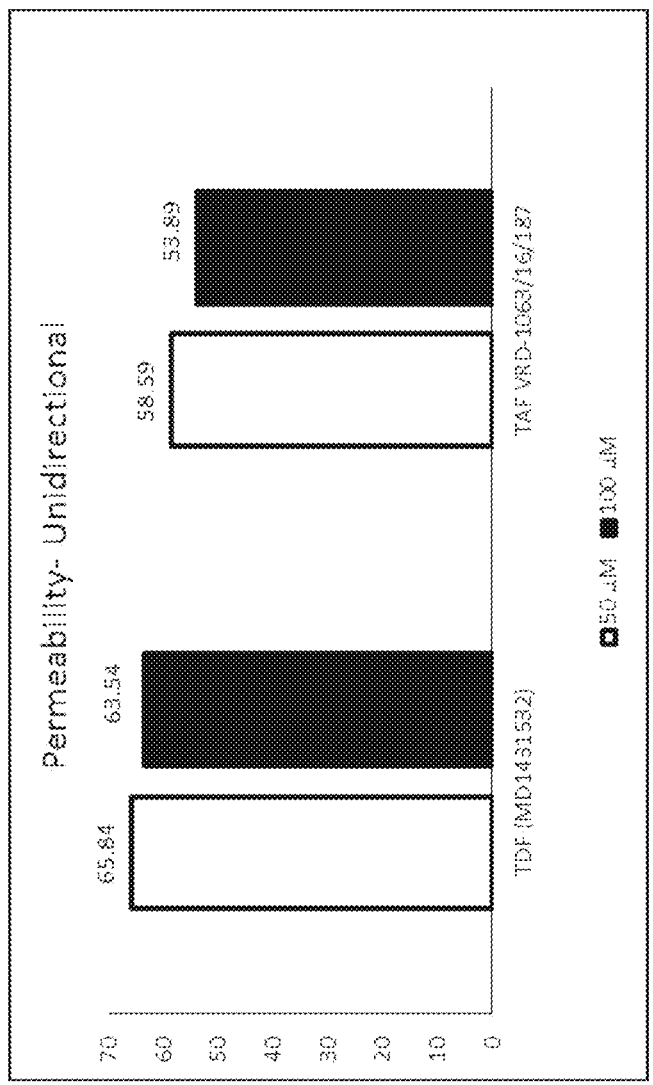
FIG. 1 depicts a bar graph of results from a unidirectional assay showing permeability of tenofovir alafenamide fumarate (TAF) and tenofovir disoproxil fumarate (TDF). TDF and TAF were observed to be low to moderately permeable drugs.

It is to be understood that the figures are not drawn or photographed to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the treatment of diseases caused by retroviruses or hepatitis B virus, especially AIDS, an HIV infection or hepatitis B, it is essential that the maximum amount of the drug reaches the site of action. Most antiretroviral drugs either have poor solubility and/or poor permeability which deteriorates the bioavailability of the drug to a major extent.

The inventors of the present invention have found ways to address the bioavailability problems of such anti-retroviral drugs. In particular, the inventors have found that, the bioavailability properties of these drugs can be improved by using a pharmacokinetic booster or enhancer.

Enhanced bioavailability of an anti-viral drug is disclosed in several references. Role of Piperine As A Bioavailability Enhancer, UMESH K PATIL et al International Journal of Recent Advances in Pharmaceutical Research October 2011; 4: 16-23 discloses piperine as a bioavailability enhancer.

WO2004067018 discloses the use of extracts of Carum carvi as bioenhancers, either alone or in combination with piperine or Zinzeber officinale extract to improve the bioavailability of zidovudine.

Natural Bioenhancers: An overview, Deepthi V. Tatiraju et al, Journal of Pharmacognosy and Phytochemistry 2013; 2 (3): 55-60. This article discloses the combination of piperine with nevirapine, wherein piperine enhanced the bioavailability of nevirapine.

Oral bioavailability enhancement of an anti-viral drug using an herbal bio-enhancer, Mohammad Asif, a dissertation submitted to the Ganpat University. This article discloses the combination of Piperine with efavirenz, wherein piperine enhanced the bioavailability of efavirenz.

Bioenhancement effect of piperine and ginger oleo resin on the bioavailability of atazanavir, Swati Prakash et al, International Journal of Pharmacy and Pharmaceutical Sciences Vol 7, Issue 10, 2015. This article discloses the combination of piperine with atazanvir, wherein piperine enhanced the bioavailability of atazanvir.

WO03084462 discloses the process for manufacturing pharmaceutical composition containing antiretroviral protease inhibitor such as indinavir, saquinavir, amprenavir, nelfinavir, lopinavir and piperine in a single pharmaceutical composition.

In some embodiments, the anti-retroviral drugs, according to the present invention, include but are not limited to Nucleoside Reverse Transcriptase Inhibitors (NRTI), Non-Nucleoside Reverse Transcriptase Inhibitors (NNRTI), Nucleotide Analog Reverse-Transcriptase Inhibitors, Protease Inhibitors (PI), Integrase Inhibitors, Fusion Inhibitors, CCR5 Inhibitors, Monoclonal Antibodies, Glycoprotein Inhibitors and any combinations thereof.

In one embodiment, the Nucleoside Reverse Transcriptase Inhibitors (NRTI) and Non-Nucleoside Reverse Transcriptase Inhibitors (NNRTI) include but are not limited to lamivudine, abacavir, zidovudine, emtricitabine didanosine, stavudine, lobucavir, entecavir, apricitabine censavudine, zalcitabine, dexelvucitabine, alovudine, efavirenz, amdoxovir, elvucitabine, festinavir, racivir, lersivirine, rilpivirine, etravirine, stampidine, Doravirine, Dapivirine.

In some embodiments, preferably, the Nucleoside Reverse Transcriptase Inhibitors (NRTI) and Non-Nucleoside Reverse Transcriptase Inhibitors (NNRTI) are abacavir, didanosine. Preferably the dose of abacavir ranges from about 3 mg to about 300 mg, and didanosine ranges from about 2 mg to about 200 mg for twice a day administration.

In another embodiment, protease inhibitors include but are not limited to lopinavir, ritonavir, saquinavir, nelfinavir, amprenavir, indinavir, nelfinavir, atazanavir, lasinavir, palinavir, tirpranavir, fosamprenavir, darunavir, or tipranavir. Preferably, the protease inhibitors are tirpranavir, darunavir. Preferably the dose of tipranavir ranges from about 5 mg to about 500 mg, and darunavir ranges from about 1 mg to about 800 mg for twice a day administration. In some embodiments, the darunavir dose ranges from about 1 mg to about 500 mg, from about 20 mg to about 500 mg, from about 25 mg to about 500 mg, from about 30 mg to about 500 mg, from about 35 mg to about 500 mg, from about 25 mg to about 35 mg, from about 50 mg to about 400 mg, or from about 100 mg to about 300 mg for twice a day administration. In some embodiments, the darunavir dose ranges from about 1 mg, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790 to about 800 mg for once a day or twice a day administration. Each dose can be in one or more unit dosage forms, as described herein.

In another embodiment, integrase inhibitors include but are not limited to dolutegravir, elvitegravir, raltegravir, bictegravir, cabotegravir. Preferably, the integrase inhibitors are elvitegravir, dolutegravir, raltegravir. Preferably the dose of Dolutegravir ranges from about 1 mg to about 50 mg, Elvitegravir ranges from about 1 mg to about 150 mg for once a day administration and that of Raltegravir ranges from about 4 mg to about 400 mg for once a day administration. In some embodiments, the dolutegravir dose ranges from about 5 mg to about 50 mg, from about 20 mg to about 50 mg, from about 25 mg to about 50 mg, from about 25 mg to about 45 mg, from about 30 mg to about 50 mg, from about 30 mg to about 40 mg, or from about 35 mg to about 50 mg for twice a day administration. In some embodiments, the dolutegravir dose ranges from about 1 mg, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mg for once a day or twice a day administration. Each dose can be in one or more unit dosage forms, as described herein.

In another embodiment, Fusion inhibitors include but are not limited to Maraviroc, Enfuvirtide, Griffithsin, Aplaviroc, Vicriviroc, Plerixafor, Fostemsavir, Albuvirtide.

In another embodiment, CCR5 inhibitors include but are not limited to Aplaviroc, Vicriviroc, Maraviroc, Cenicriviroc.

In another embodiment, Monoclonal Antibodies include but are not limited to Ibalizumab.

In another embodiment, Glycoprotein Inhibitors include but are not limited to Sifuvirtide.

In another embodiment, Nucleotide Analog Reverse-Transcriptase Inhibitors include but are not limited to tenofovir alafenamide fumarate, tenofovir disoproxil fumarate and adefovir. Preferably, the Nucleotide Analog Reverse-Transcriptase Inhibitors are tenofovir alafenamide fumarate and tenofovir disoproxil fumarate. In some embodiments, the tenofovir alafenamide fumarate dose ranges from about 1 mg to about 25 mg, from about 2.5 mg to about 25 mg, from about 5 mg to about 20 mg, or from about 5 mg to about 15 mg for twice a day administration. In some embodiments, the tenofovir alafenamide fumarate dose ranges from about 1 mg, 2, 3, 4, 5, 6, 7, 8, 9, 10, 11, 12, 13, 14, 15, 16, 17, 18, 19, 20, 21, 22, 23, 24 to about 25 mg for once a day or twice a day administration. In some embodiments, the tenofovir disoproxil fumarate dose ranges from about 1 mg to about 300 mg, from about 1 mg to about 150 mg, from about 75 mg to about 250 mg, from about 100 mg to about 200 mg, or from about 120 to about 180 mg for twice a day administration. In some embodiments, the tenofovir disoproxil fumarate dose ranges from about 1 mg, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290 to about 300 mg for once a day or twice a day administration. Each dose can be in one or more unit dosage forms, as described herein.

The term "Anti-retroviral drug" and "Pharmacokinetic booster or enhancer" is used in broad sense to include not only "Anti-retroviral drug" per se and "Pharmacokinetic booster or enhancer" per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

The term "pharmacokinetic booster or enhancer" is an alkaloid. In some embodiments, the pharmacokinetic booster or enhancer comprises piperine, tetrahydropiperine, cis-piperine, trans-piperine, cis-trans piperine, trans,cis-piperine, cis,cis-piperine, trans,trans-piperine or a combination thereof. More preferably, the pharmacokinetic booster or enhancer is piperine or tetrahydropiperine and its analogs or derivatives. In some embodiments, the pharmacokinetic booster or enhancer increases plasma concentrations of the anti-retroviral drug by 10%, 20, 30, 40, 50, 60, 70, 80, 90, 100% or higher in comparison to when the pharmacokinetic booster or enhancer is not used.

The term "injectable" is a mode of administering the pharmaceutical composition. The pharmaceutical composition can be administered in a variety of ways. In humans, the pharmaceutical composition can be administered by the parenteral route. For example, the pharmaceutical composition can be administered intravenously (e.g., intravenous injection), subcutaneously, intradermally, or by intramuscular injection. Intravenous administration can be accomplished by mixing the pharmaceutical composition in a suitable pharmaceutical carrier (vehicle) or excipient as understood by practitioners in the art. Formulations suitable for parenteral administration conveniently comprise a sterile aqueous preparation of the pharmaceutical composition, which can be formulated to be isotonic with the blood of the patient.

The term "therapeutically effective amount" or "effective amount" is such that when administered, the pharmaceutical composition results in the inhibition of a virus or disease. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired.

The term "treatment" or "treating" of a disease, virus or condition refers to executing a protocol that may include administering one or more drugs to a patient, in an effort to alleviate signs or symptoms of the disease, virus or condition. Alleviation can occur prior to signs or symptoms of the disease, virus or condition appearing, as well as after their appearance. Thus, treating or treatment includes reducing, preventing or prevention of the disease, virus or condition. In addition, treating or treatment does not require complete alleviation of signs or symptoms, does not require a cure, and specifically includes protocols that have only a marginal effect on the patient.

The fruit of black pepper (*Piper nigrum* L.) and long pepper (*Piper longum* L.) are both important medicinal herbs in Ayurvedic and Unani (traditional Indian) systems of medicine, wherein the remedy generally consists of mixtures of herbs. A wide range of the medicinal uses of black pepper are known and have been documented including its use in the treatment of leucoderma.

Piperine, can be the pharmacokinetic booster or enhancer. Piperine, the major alkaloid found in the fruit of black pepper (*Piper nigrum* L.; *Piperaceae*), stimulates the replication of melanocytes and induces the formation of melanocytic dendrites. Piperine is expected to cause the repopulation of vitiligo patches through a stimulatory effect on perilesional and follicular melanocytes.

Piperine is chemically known as (1-2E, 4E-piperinoyl-piperidine) and is structurally represented as shown below.

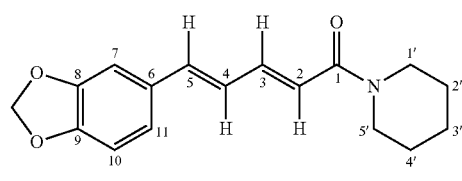

Piperine [E,E-(trans-trans)-piperine]

Piperine may enhance the drug bioavailability by promoting rapid absorption of drugs and nutrients by increasing blood supply to the gastrointestinal tract, decreasing hydrochloric acid secretion to prevent the breakdown of some drugs, increasing the emulsifying content of the gut, increasing enzymes like γ-glutamyl transpeptidase which participate in active and passive transport of nutrients to the intestinal cells.

Piperine may increase the drug bioavailability by inhibiting enzymes which participate in the biotransformation of drugs and thus preventing their inactivation and elimination. It also inhibits p-glycoprotein, the 'pump' protein that removes substances from cells and can decrease the intestinal production of glucuronic acid, thereby permitting more substances to enter the body in active form.

Piperine has also been reported to occur in other *Piper* species i.e. *P. acutisleginum, album, argyrophylum, attenuatum, aurantiacum, betle, callosum, chaba, cubeba, guineense, hancei, khasiana, longum, macropodum, nepalense, novae hollandiae, peepuloides, retrokacturn*, and *sylvaticum*.

Tetrahydropiperine is a structural analog of Piperine. The two double bonds at position 2 and 4 are saturated to give a tetrahydro analog. Tetrahydropiperine is chemically known as 5-(1,3-benzodioxol-5-yl)-1-piperidin-1-ylpentan-1-one and is structurally represented as shown below.

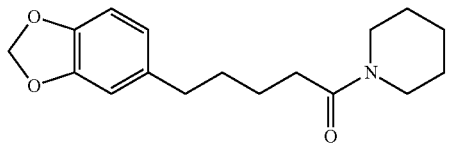 [SMILES: O=C(CCCCc1ccc2c(c1)OCO2)N1CCCCC1]

Tetrahydropiperine occurs like piperine naturally in black pepper (about 0.7% in black pepper oleoresin). Tetrahydropiperine can be synthesized from piperine which is previously extracted from black pepper oleoresin.

The term "analogs or derivatives" of tetrahydropiperine is used in broad sense to include alkyltetrahydropiperines, e.g. methyltetrahydropiperine or ethyltetrahydropiperine, dialkyltetrahydropiperines, e.g. dimethyltetrahydropiperine or diethyltetrahydropiperine, alkoxylated tetrahydropiperine, e.g. methoxy tetrahydropiperine, hydroxylated tetrahydropiperine, e.g. 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, halogenated tetrahydropiperine, e.g. 1-[(5,3-benzodioxyl-5-yl)-1-oxo-4-halo-2-pentenyl]-piperine and 1-[(5,3-benzodioxyl-5-yl)-1-oxo-2-halo-4-pentenyl]-piperine, dihydropiperine, alkyldihydropiperines, e.g. methyldihydropiperine or ethyldihydropiperine, dialkyldihydropiperines, e.g. dimethyldihydropiperine or diethyldihydropiperine, alkoxylated dihydropiperine, e.g. methoxy dihydropiperine, and halogenated dihydropiperine and their pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

In some embodiments, preferably the dose of piperine ranges from about 0.5 mg to about 400 mg and the dose of tetrahydropiperine ranges from about 0.5 mg to about 400 mg. In some embodiments, the dose of the piperine and/or the tetrahydropiperine ranges from about 0.5 mg, 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, to about 400 mg. In some embodiments, the ratio of the at least one anti-retroviral drug to the at least one pharmacokinetic booster or enhancer is from about 100:1 to about 1:1 by weight.

Preferably, the pharmaceutical composition may be provided in dosage forms such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, lyophilized powder, modified release formulations, delayed release formulations, extended release formulations, pulsatile release formulations, dual release formulations and the like. Liquid, liquid injectable or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention. In some embodiments, the pharmaceutical composition is administered via a syrup. A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

In some embodiments, a unit dosage from, such as a tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

The pharmaceutical compositions of the present invention comprise at least one anti-retroviral drug and piperine or tetrahydropiperine. These active ingredients are formulated for simultaneous, separate or sequential administration. When the active ingredients are administered sequentially, either at least one anti-retroviral drug or piperine/tetrahydropiperine, may be administered first. When administration is simultaneous, the active ingredients may be administered either in the same or different pharmaceutical compositions. Adjunctive therapy, e.g., where one active ingredient is used as the primary treatment and the other active ingredient(s) is/are used to assist that primary treatment is also an embodiment of the present invention.

Accordingly, there is provided a product comprising at least one anti-retroviral drug and piperine or tetrahydropiperine as a combined preparation for simultaneous, separate or sequential use for treatment of diseases caused by retroviruses or hepatitis B virus, especially AIDS or an HIV infection, or hepatitis B.

In some embodiments, the pharmaceutical compositions of the present invention comprise tenofovir disproxil fumarate and piperine for the treatment of diseases caused by retroviruses, especially Acquired Immune Deficiency Syndrome or an HIV infection.

According to a preferred embodiment, the pharmaceutical compositions of the present invention comprise tenofovir disproxil fumarate and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir alafenamide fumarate and piperine for the treatment of diseases caused by retroviruses, especially AIDS or an HIV infection.

According to a preferred embodiment, the pharmaceutical compositions of the present invention comprise tenofovir alafenamide fumarate and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise dolutegravir and piperine for the treatment of diseases caused by retroviruses, especially Acquired Immune Deficiency Syndrome or an HIV infection.

According to a preferred embodiment, the pharmaceutical compositions of the present invention comprise dolutegravir and piperine in a ratio from about from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise darunavir and piperine for the treatment of diseases caused by retroviruses, especially Acquired Immune Deficiency Syndrome or an HIV infection.

According to a preferred embodiment, the pharmaceutical compositions of the present invention comprise darunavir and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir disproxil fumarate and piperine for treatment of diseases caused by hepatitis B virus.

According to a preferred embodiment, the pharmaceutical compositions of the present invention comprise tenofovir disproxil fumarate and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir alafenamide fumarate and piperine for treatment of diseases caused by hepatitis B virus.

According to a preferred embodiment, the pharmaceutical compositions of the present invention comprise tenofovir alafenamide fumarate and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir disproxil fumarate and tetrahydropiperine for the treatment of diseases caused by retroviruses, especially Acquired Immune Deficiency Syndrome or an HIV infection.

According to a preferred embodiment, the pharmaceutical compositions of the present invention comprise tenofovir disproxil fumarate and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir alafenamide fumarate and tetrahydropiperine for the treatment of diseases caused by retroviruses, especially Acquired Immune Deficiency Syndrome or an HIV infection.

According to a preferred embodiment, the pharmaceutical compositions of the present invention comprises tenofovir alafenamide fumarate and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise dolutegravir and tetrahydropiperine for the treatment of diseases caused by retroviruses, especially Acquired Immune Deficiency Syndrome or an HIV infection.

According to a preferred embodiment, the pharmaceutical compositions of the present invention comprises dolutegravir and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise darunavir and tetrahydropiperine for the treatment of diseases caused by retroviruses, especially Acquired Immune Deficiency Syndrome or an HIV infection.

According to a preferred embodiment, the pharmaceutical compositions of the present invention comprises darunavir and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir disproxil fumarate and tetrahydropiperine for treatment of diseases caused by hepatitis B virus.

According to a preferred embodiment, the pharmaceutical compositions of the present invention comprises tenofovir disproxil fumarate and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprise tenofovir alafenamide fumarate and tetrahydropiperine for treatment of diseases caused by hepatitis B virus.

According to a preferred embodiment, the pharmaceutical compositions of the present invention comprises tenofovir alafenamide fumarate and tetrahydropiperine in a ratio from about 100:1, 50:1, 40:1, 30:1, 20:1, 10:1, 8:1, 6:1, 5:1, 4:1, 3:1, 2:1, to about 1:1 by weight.

In some embodiments, when the pharmacokinetic booster or enhancer or derivative thereof is administered with the anti-retroviral drug in the pharmaceutical composition, a dosing frequency of the at least one anti-retroviral drug that is administered to a patient is reduced. In some embodiments, the at least one pharmacokinetic booster or enhancer or derivative thereof increases the bioavailability of the at least one anti-retroviral drug from about 10% to about 100%, from about 10% to about 70%, from about 10% to about 50%, from about 10% to about 30%, or from about 10% to about 20%. In some embodiments, the at least one pharmacokinetic booster or enhancer or derivative thereof increases the bioavailability of the at least one anti-retroviral drug from about 10%, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

The inventors of the present invention have also found that the bioavailability properties of anti-retroviral drugs may also be improved by nanosizing. In some embodiments, the pharmaceutical composition is administered via nanoparticles having a size of about 1 nanometer (nm) to about 50 nm. In some embodiments, the nanoparticles have a size of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nm.

In some embodiments, suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some embodiments, when the pharmaceutical composition is provided in unit dosage forms, as discussed above, the unit dosage form can be uncoated or coated.

These and other aspects of the present application will be further appreciated upon consideration of the following Examples, which are intended to illustrate certain particular embodiments of the application but are not intended to limit its scope, as defined by the claims.

EXAMPLES

Example 1

TABLE 1

| Ingredient | Tab (%) |
|---|---|
| Dry mix | |
| Tenofovir Alafenamide Fumarate | 0.1%-10% |
| Emtricitabine | 25%-40% |
| Piperine | 0.1%-10% |
| Lactose | 5%-40% |
| Colloidal silicon dioxide | 1%-10% |
| Microcrystalline Cellulose | 1%-15% |
| Croscarmellose Sodium | 1%-10% |
| Magnesium Stearate | 0.5%-10% |
| Blending & Lubrication | |
| Colloidal silicon dioxide | 1%-10% |
| Microcrystalline Cellulose | 1%-15% |
| Croscarmellose Sodium | 1%-10% |
| Magnesium Stearate | 0.5%-10% |
| Film Coating | |
| Opadry | 1%-10% |

Process:

1) Tenofovir alafenamide fumarate, emtricitabine, piperine, lactose, colloidal silicon dioxide, microcrystalline cellulose and croscarmellose sodium were dry mixed in a suitable blender.

2) The blend obtained in step (1) was lubricated with magnesium stearate and was compacted and dry granulated.

3) The granules obtained in step (3), colloidal silicon dioxide, microcrystalline cellulose and croscarmellose sodium were mixed to form a blend.

4) The blend obtained in step (3) was compressed to form tablets and coated with Opadry.

Example 2

TABLE 2

| Ingredient | Tab wt. % |
|---|---|
| Dry mix | |
| Tenofovir Alafenamide Fumarate | 0.1%-10% |
| Piperine | 0.1%-10% |
| Lactose | 5%-40% |
| Microcrystalline Cellulose | 1%-15% |
| Croscarmellose Sodium | 1%-10% |
| Lubrication | |
| Magnesium Stearate | 0.5%-10% |
| Film Coating | |
| Opadry | 1%-10% |

Process:

1) Tenofovir alafenamide fumarate, piperine, lactose, colloidal silicon dioxide, microcrystalline cellulose and croscarmellose sodium were dry mixed in a suitable blender.

2) The blend obtained in step (1) was lubricated with magnesium stearate, compressed to form tablets and coated with Opadry.

Example 3

TABLE 3

| Ingredient | Tab wt. % |
|---|---|
| Dry mix | |
| Tenofovir Alafenamide Fumarate | 0.1%-10% |
| Emtricitabine | 25%-40% |
| Piperine | 0.1%-10% |
| Elvitegravir | 10%-30% |
| Lactose | 5%-40% |
| Colloidal silicon dioxide | 1%-10% |
| Microcrystalline Cellulose | 1%-15% |
| Croscarmellose Sodium | 1%-10% |
| Magnesium Stearate | 1%-10% |
| Blending & Lubrication | |
| Colloidal silicon dioxide | 1%-10% |
| Microcrystalline Cellulose | 1%-15% |
| Croscarmellose Sodium | 1%-10% |
| Magnesium Stearate | 1%-10% |
| Film Coating | |
| Opadry | 1%-10% |

Process:

1) Tenofovir alafenamide fumarate, emtricitabine, piperine, elvitegravir, lactose, colloidal silicon dioxide, croscarmellose sodium and microcrystalline cellulose were dry mixed to obtain a blend.

2) The blend obtained in step (1) was lubricated with magnesium stearate, compacted, sized compressed to form tablets.

Example 4

TABLE 4

| Ingredient | Tab wt. % |
|---|---|
| Dry mix | |
| Tenofovir Disoproxil Fumarate | 10%-40% |
| Emtricitabine | 25%-40% |
| Piperine | 0.1%-10% |
| Elvitegravir | 10%-30% |
| Lactose | 5%-40% |
| Colloidal silicon dioxide | 1%-10% |
| Microcrystalline Cellulose | 1%-15% |
| Croscarmellose Sodium | 1%-10% |
| Magnesium Stearate | 1%-10% |
| Blending & Lubrication | |
| Colloidal silicon dioxide | 1%-10% |
| Microcrystalline Cellulose | 1%-15% |
| Croscarmellose Sodium | 1%-10% |
| Magnesium Stearate | 1%-10% |
| Film Coating | |
| Opadry | 1%-10% |

Process:

Tenofovir disoproxil fumarate, emtricitabine, piperine, elvitegravir, lactose, colloidal silicon dioxide, croscarmellose sodium and microcrystalline cellulose were dry mixed to obtain a blend.

2) The blend obtained in step (1) was lubricated with magnesium stearate, compacted, sized compressed to form tablets.

Example 5

TABLE 5

| Sr. No. | Ingredients | Qty/Unit (mg) |
|---|---|---|
| 1. | Dolutegravir Sodium | 5-50 |
| 2. | Piperine | 0.1-50 |
| 3. | Mannitol | 10-75 |
| 4. | Povidone | 2-20 |
| 5. | Sodium Starch Glycolate | 5-20 |
| 6. | Mannitol | 50-150 |
| 7. | Microcrystalline cellulose | 20-100 |
| 8. | Colloidal silicon dioxide | 0.1-2 |
| 9. | Sodium Stearyl Fumarate | 0.5-10 |
| 10. | Coating pre-mix | 1-20 |

Process:

Dolutegravir sodium, Piperine, Mannitol were dry mixed and Povidone was dissolved in water.

2) The dry mix obtained in step (1) was granulated and the granules obtained were milled.

3) The granules obtained in step (2) were blended with mannitol, sodium starch glycolate, microcrystalline cellulose and colloidal silicon dioxide.

4) The blend obtained in step (3) was lubricated with Sodium stearyl fumarate, compressed and coated.

Example 6

TABLE 6

| Sr. No. | Ingredients | Mg/Tab |
|---|---|---|
| 1 | Darunavir Hydrate | 50-651 |
| 2 | Piperine | 5-100 |
| 3 | Microcrystalline Cellulose | 50-540 |
| 4 | Crospovidone | 0-25 |
| 5 | Colloidal silicon dioxide | 0.5-25 |
| 6 | Magnesium Stearate | 0.1-10 |
| | Film Coating | |
| 7 | Opadry | 5-50 |
| 8 | Purified Water | qs |

Process:

1) Darunavir hydrate, Piperine, microcrystalline cellulose, Crospovidone & Colloidal silicon dioxide were sifted and mixed.

2) The dry mix obtained in step (1) was granulated and lubricated with magnesium stearate.

3) The granules obtained in step (2) were compressed and coated with Opadry.

Example 7

TABLE 7

| Sr. No. | Ingredients | Qty/Unit (mg) |
|---|---|---|
| 1 | Darunavir Hydrate | 50-870 |
| 2 | Piperine | 0.5-250 |
| 3 | Povidone | 0.1-15 |
| 4 | Microcrystalline Cellulose | 10-280 |
| 5 | Crospovidone | 0.5-35 |
| 6 | Colloidal Silicon Dioxide | 0-7.0 |
| 7 | Magnesium Stearate | 0.1-9.0 |
| | Film Coating | |
| 8 | Opadry | 10-50 |
| 9 | Purified Water | q. s. |

Process:

1) Darunavir hydrate, Piperine, povidone, microcrystalline cellulose, Crospovidone & Colloidal silicon dioxide were sifted and mixed.

2) The dry mix obtained in step (1) was granulated and lubricated with magnesium stearate.

3) The granules obtained in step (2) were compressed and coated with Opadry.

Example 8

TABLE 8

| Sr. No | Ingredients | Qty/Unit (mg) |
|---|---|---|
| 1 | Darunavir Ethanolate | 50-651 |
| 2 | Piperine | 5-300 |
| 2 | Silicified Microcrystalline Cellulose | 10-551 |
| 3 | Colloidal Silicon Dioxide | 0-25 |
| 4 | Crospovidone | 0.2-15 |
| 5 | Magnesium Stearate | 0.1-10 |
| | Film Coating | |

TABLE 8-continued

| Sr. No | Ingredients | Qty/Unit (mg) |
|---|---|---|
| 7 | Opadry | 5-50 |
| 8 | Purified Water | q. s. |
|  | Total |  |

Process:

Darunavir ethanolate, Piperine, povidone, silicified microcrystalline cellulose, Crospovidone & Colloidal silicon dioxide were sifted and mixed.

2) The dry mix obtained in step (1) was granulated and lubricated with magnesium stearate.

3) The granules obtained in step (2) were compressed and coated with Opadry.

Example 9

TABLE 9

| Sr. No. | Ingredients | Qty/Unit (mg) |
|---|---|---|
| 1. | Darunavir Ethanolate | 50-870 |
| 2 | Piperine | 5-400 |
| 3 | Hydroxy propyl methyl cellulose | 0.1-15 |
| 4. | Silicified Microcrystalline cellulose | 10-180 |
| 5. | Crospovidone | 0.1-40 |
| 6. | Colloidal silicon dioxide | 0-5.0 |
| 7. | Magnesium stearate | 0.1-10 |
|  | Film coating |  |
| 8. | Opadry | 5-40 |
| 9. | Purified water | q.s. |

Process:

1) Darunavir ethanolate, Piperine, Hydroxy propyl methyl cellulose, silicified microcrystalline cellulose, Crospovidone & Colloidal silicon dioxide were sifted and mixed.

2) The dry mix obtained in step (1) was granulated and lubricated with magnesium stearate.

3) The granules obtained in step (2) were compressed and coated with Opadry.

Example 10

TABLE 10

| Sr. No. | Ingredients | Qty/Tab (mg) |
|---|---|---|
|  | Dry Mix (Lamivudine Part) |  |
| 1. | Lamivudine | 300.00 |
| 2. | Microcrystalline cellulose | 50.80 |
| 3. | Croscarmellose sodium | 22.50 |
| 4. | Pregelatinized starch | 18.00 |
| 5. | Magnesium Stearate | 2.50 |
|  | Dry Mix (Tenofovir Disoproxil Fumarate Part) |  |
| 6. | Tenofovir Disoproxil Fumarate | 100.00 |
| 7 | Piperine | 20.00 |
| 8. | Microcrystalline cellulose | 45.20 |
| 9. | Croscarmellose sodium | 22.50 |
| 10. | Magnesium Stearate | 2.50 |
|  | Blending and Lubrication |  |
| 11. | Croscarmellose sodium | 30.00 |
| 12. | Microcrystalline cellulose | 100.00 |
| 13. | Magnesium Stearate | 6.00 |
|  | Total | 720.00 |
|  | Seal Coating |  |
| 14. | Hypromellose | 5.00 |
| 15. | Isopropyl Alcohol | q.s |
| 16. | Purified water | q.s |
|  | Total | 725.00 |
|  | Film Coating |  |
| 17. | Opadry II 85G18490 White | 22.00 |
| 18. | Purified water | q.s |
|  | Final Tablet weight | 747.00 |

Process:

1) Lamivudine, Microcrystalline cellulose, Croscarmellose sodium, Pregelatinised starch and magnesium stearate was blended and compacted into granular mass.

2) Tenofovir disoproxil fumarate, Piperine, Microcrystalline cellulose, Croscarmellose sodium and magnesium stearate was blended and compacted into granular mass.

3) Microcrystalline cellulose, Croscarmellose sodium and magnesium stearate was mixed with the blends obtained in step (1) and step (2) and compressed to form tablets with seal coating followed by film coating.

Example 11

TABLE 11

| Sr. No. | Ingredients | Qty/Tab (mg) |
|---|---|---|
|  | Dry Mix (Emtricitabine, TDF & Piperine part) |  |
| 1. | Emtricitabine | 200.000 |
| 2. | Tenofovir Disoproxil Fumarate | 100.000 |
| 3. | Piperine | 20.00 |
| 4. | Lactose monohydrate | 80.000 |
| 5. | Croscarmellose Sodium | 30.000 |
| 6. | Microcrystalline cellulose | 300.000 |
| 7. | Magnesium Stearate | 4.000 |
|  | Blending and Lubrication |  |
| 8. | Croscarmellose sodium | 30.00 |
| 9. | Microcrystalline cellulose | 100.00 |
| 10. | Magnesium Stearate | 6.00 |
|  | Rilpivirine Part (Binder Slurry) |  |
| 11. | Rilpivirine Hydrochloride | 27.500 |
| 12. | Lactose monohydrate | 13.000 |
| 13. | Povidone | 3.250 |
| 14. | Polysorbate 20 | 0.350 |
| 15. | Purified water | 110 |
|  | Granulation |  |
| 16. | Lactose monohydrate | 50.000 |
| 17. | Crospovidone | 5.000 |

TABLE 11-continued

| Sr. No. | Ingredients | Qty/Tab (mg) |
|---|---|---|
| | Blending and Lubrication | |
| 18. | Crospovidone | 3.000 |
| 19. | Silicified Microcrystalline cellulose | 16.800 |
| 20. | Magnesium stearate | 1.100 |
| | Film Coating | |
| 21. | Opadry II 85G18490 White | 30.00 |
| 22. | Purified water | q.s |
| | Final Tablet weight | 1020.00 |

Process:

1) Emtricitabine, Tenofovir disoproxil fumarate, piperine, Lactose monohydrate, Microcrystalline cellulose, Croscarmellose sodium and magnesium stearate was blended and compacted into granular mass.

2) Microcrystalline cellulose, Croscarmellose sodium and magnesium stearate was blended and compacted into granular mass.

3) Polysorbate 80, Povidone and lactose was dissolved in water.

4) Rilpivirine was added to the solution in obtained in step (3) to form a slurry.

5) Dry mix of lactose monohydrate and crospovidone was added to the slurry obtained in step (4).

6) Microcrystalline cellulose, Crospovidone and magnesium stearate was added to the dry blend obtained in step (5).

7) The blend obtained in step (1) was compressed with the blend obtained in step (6) to form a bilayer tablet with film coating.

Example 12

TABLE 12

| Sr. No. | Ingredients | Qty/Tab (mg) |
|---|---|---|
| | Dry Mix | |
| 1. | Emtricitabine | 200.000 |
| 2. | Tenofovir Disoproxil Fumarate | 100.000 |
| 3. | Piperine | 20.00 |
| 4. | Lactose monohydrate | 80.000 |
| 5. | Croscarmellose Sodium | 30.000 |
| 6. | Microcrystalline cellulose | 300.000 |
| 7. | Magnesium Stearate | 4.000 |
| | Blending and Lubrication | |
| 8. | Croscarmellose sodium | 30.00 |
| 9. | Microcrystalline cellulose | 100.00 |
| 10. | Magnesium Stearate | 6.00 |
| | Total | 870.00 |
| | Film Coating | |
| 11. | Opadry II 85G18490 White | 30.00 |
| 12. | Purified water | q.s |
| | Final Tablet weight | 900.00 |

Process:

1) Emtricitabine, Tenofovir disoproxil fumarate, piperine, Lactose monohydrate, Microcrystalline cellulose, Croscarmellose sodium and magnesium stearate were mixed and blended to form a granular mass.

2) Microcrystalline cellulose, Croscarmellose sodium and magnesium stearate were mixed and blended.

3) The blend obtained in step (1) and step (2) was compressed and coated to form tablets with film coating.

Example 13

TABLE 13

| Sr. No. | Ingredients | Qty/Tab (mg) |
|---|---|---|
| | Dry Mix (Emtricitabine + Piperine + TDF Part) | |
| 1. | Emtricitabine | 200.000 |
| 2. | Tenofovir Disoproxil Fumarate | 100.000 |
| 3. | Piperine | 20.00 |
| 4. | Lactose monohydrate | 80.000 |
| 5. | Croscarmellose Sodium | 30.000 |
| 6. | Microcrystalline cellulose | 300.000 |
| 7. | Magnesium Stearate | 4.000 |
| | Blending and Lubrication | |
| 8. | Croscarmellose sodium | 30.00 |
| 9. | Microcrystalline cellulose | 100.00 |
| 10. | Magnesium Stearate | 6.00 |
| | Weight of Emtricitabine, piperine & TDF Layer | 870.00 |
| | Dry Mix (Efavirenz Part) | |
| 11. | Efavirenz | 600.00 |
| 12. | Microcrystalline cellulose | 202.00 |
| 13. | Sodium lauryl sulphate | 6.00 |
| 14. | Croscarmellose sodium | 48.00 |
| 15. | Hydroxypropyl cellulose | 38.40 |
| 16. | Purified water | qs |
| | Blending and Lubrication | |
| 17. | Lactose Monohydrate | 199.60 |
| 18. | Magnesium Stearate | 6.00 |
| 19. | Weight of Efavirenz layer | 1100 |
| | Total weight of uncoated tablet | 1970 |
| | Seal Coating | |
| 20. | Hypromellose | 10.00 |
| 21. | Isopropyl Alcohol | q.s |
| 22. | Purified water | q.s |
| | Total | 1980.00 |
| | Film Coating | |
| 23. | Opadry II 85G18490 White | 60.00 |
| 24. | Purified water | q.s |
| | Final Tablet weight | 2040.00 |

Process:

1) Emtricitabine, Tenofovir disoproxil fumarate, piperine, Lactose monohydrate, Microcrystalline cellulose, Croscarmellose sodium and magnesium stearate were mixed and blended to form a granular mass.

2) Microcrystalline cellulose, Croscarmellose sodium and magnesium stearate were added to the blend obtained in step (1) and further blended.

3) Efavirenz, microcrystalline cellulose and croscarmellose sodium were added to SLS followed by Hydroxypropyl cellulose to form a solution and granulated.

4) Lactose monohydrate and magnesium stearate were blended and compressed to form a bilayer tablet having with film coating.

Example 14

TABLE 14

| Sr. No. | Ingredients | Qty/Tab (mg) |
|---|---|---|
|  | Dry Mix (Lamivudine Part) |  |
| 1. | Lamivudine | 300.00 |
| 2. | Microcrystalline cellulose | 50.80 |
| 3. | Croscarmellose sodium | 22.50 |
| 4. | Pregelatinized starch | 18.00 |
| 5. | Magnesium Stearate | 2.50 |
|  | Dry Mix (Tenofovir Disoproxil Fumarate Part) |  |
| 6. | Tenofovir Disoproxil Fumarate | 100.00 |
| 7 | Piperine | 20.00 |
| 8. | Microcrystalline cellulose | 45.20 |
| 9. | Croscarmellose sodium | 22.50 |
| 10. | Magnesium Stearate | 2.50 |
|  | Blending and Lubrication |  |
| 11. | Croscarmellose sodium | 30.00 |
| 12. | Microcrystalline cellulose | 100.00 |
| 13. | Magnesium Stearate | 6.00 |
|  | Weight of Lamivudine, piperine & TDF Layer | 720.00 |
|  | Dry Mix (Efavirenz Part) |  |
| 14. | Efavirenz | 600.00 |
| 15. | Microcrystalline cellulose | 202.00 |
| 16. | Sodium lauryl sulphate | 6.00 |
| 17. | Croscarmellose sodium | 48.00 |
| 18. | Hydroxypropyl cellulose | 38.40 |
| 19. | Purified water | qs |
|  | Blending and Lubrication |  |
| 20. | Lactose Monohydrate | 199.60 |
| 21. | Magnesium Stearate | 6.00 |
|  | Weight of Efavirenz layer | 1100 |
|  | Total weight of uncoated tablet | 1820 |
|  | Seal Coating |  |
| 22. | Hypromellose | 10.00 |
| 23. | Isopropyl Alcohol | q.s |
| 24. | Purified water | q.s |
|  | Total | 1820.00 |
|  | Film Coating |  |
| 25. | Opadry II 85G18490 White | 55.00 |
| 26. | Purified water | q.s |
|  | Final Tablet weight | 1875.00 |

Process:

1) Lamivudine, Microcrystalline cellulose, Croscarmellose sodium, Pregelatinised starch and magnesium stearate was blended to form a granular mass.

2) Tenofovir disoproxil fumarate, Piperine, Microcrystalline cellulose, Croscarmellose sodium and magnesium stearate was blended to form a granular mass.

3) Microcrystalline cellulose, Croscarmellose sodium and magnesium stearate was mixed with the blends obtained in step (1) and step (2).

4) Efavirenz, microcrystalline cellulose and croscarmellose sodium were added to SLS followed by Hydroxypropyl cellulose to form a solution and granulated.

5) Lactose monohydrate and magnesium stearate were blended and compressed to form a bilayer tablet having with seal coating followed by film coating.

In order that this invention be more fully understood, the following preparative and testing methods are set forth. These methods are for the purpose of illustration only and are not to be construed as limiting the scope of the invention in any way.

Preparative and Testing Methods

I) Material

Caffeine (high permeable marker), Atenolol (low permeable marker), Digoxin (known P-gp substrate), TDF (MD1431532), TAF (VRD-1063/16/187), HBSS buffer, MES hydrate, HEPES powder, Fetal bovine serum (FBS), Minimum essential medium (MEM), Lucifer yellow, Piperine (P-gp inhibitor)

Method

1) Caco-2 Cell Culture

Caco-2 cells were cultured in MEM media with 10% serum and seeded at a density of 75000 cells per mL and cultured for 21 days in a 24-well trans-well plate at 37° C., 5% $CO_2$. The monolayer integrity was checked intermittently (Day 0-21) using Trans Epithelial Electric Resistance (TEER). Cells were treated with drugs as follows:

2) Unidirectional Assay (A-B)

Stock preparations: 10 mM stocks of all the drugs were prepared in DMSO. The test concentrations were further prepared in HBSS buffer containing 10 mM MES hydrate pH 6.8 as per the plate plan. Also, HBSS buffer with 10 mM HEPES with pH 7.4 was prepared.

Study Plan

Plate Setup

TABLE 15

|  | 1 | 2 | 3 |
|---|---|---|---|
| A | Caffeine 10 μM (A-B) | TDF 50 μM (A-B) | TAF 50 μM (A-B) |
| B |  |  |  |
| C | Atenolol 50 μM (A-B) | TDF 100 μM (A-B) | TAF 100 μM (A-B) |
| D |  |  |  |
| Batch no | Positive control | MD1431532 | VRD-1063/16/187 |

Assay Protocol

0400 μL samples were added to the wells as per the plate setup to the apical side (A) prepared in 10 mM MES hydrate pH 6.8 in duplicates and 800 μL HBSS with 10 mM HEPES pH 7.4 was added to all basal wells (B). Samples were collected at 60, 90 and 120 minutes from the basal side. Mass balance samples at 0 and 120 minutes were collected from the apical side. The sample were analyzed on LCMS-MS.

4) Bidirectional assay (A-B and B-A) to study the effect of piperine (P-gp inhibitor) on the permeability Plate Plan

TABLE 16

|   | 1 | 2 | 3 | 4 | 5 | 6 |
|---|---|---|---|---|---|---|
| A | Digoxin 10 µM A-B | Digoxine 10 µM (A-B) + Piperine 10 µM A-B | TAF 100 µM (VRD-1063/16/187) A-B | TAF 100 µM (VRD-1063/16/187) + Piperine 0.1 µM A-B | TAF 100 µM (VRD-1063/16/187) + Piperine 1 µM A-B | TAF 100 µM (VRD-1063/16/187) + Piperine 10 µM A-B |
| B |   |   |   |   |   |   |
| C | Digoxin 10 µM B-A | Digoxin 10 µM (B-A) + Piperine 10 µM B-A | TAF 100 µM (VRD-1063/16/187) B-A | TAF 100 µM (VRD-1063/16/187) + Piperine 0.1 µM B-A | TAF 100 µM (VRD-1063/16/187) + Piperine 1 µM B-A | TAF 100 µM (VRD-1063/16/187) + Piperine 10 µM B-A |
| D |   |   |   |   |   |   |

Assay Protocol

400 µL samples were added to the wells as per the plate setup to the apical side in duplicates with 800 µL HBSS pH 7.4 in the basal wells. Samples were collected at 60, 90 and 120 minutes from the basal side. Mass balance samples at 0 and 120 minutes were collected from the apical side.

For B-A, 800 µL of the respective dilutions were added to the basal side in duplicates with 400 µL HBSS pH 7.4 in the apical wells. Samples were collected at 60, 90 and 120 minutes from the apical side. Mass balance samples at 0 and 120 minutes were collected from the basal side. The sample were analyzed on LCMS-MS.

At the end of the experiment the monolayer integrity was checked using Lucifer yellow, and calculating the % rejection of Lucifer yellow by incubating cells with 100 µg/mL Lucifer.

5) Data Analysis:

Papp was calculated as follows:

The apparent permeability (Papp) in units per second can be calculated by using the following equation, For single point method:

$$Papp = (V/(T*A))*(C0/Ct)$$

For multi-point method:

$$Papp = (dQ/dt)/(A*C0)$$

$$\% \text{ Mass balance} = 100 - [CR120*VR + CD120*VD/C0*VD]$$

For Lucifer yellow, $$\% \text{ Lucifer Yellow Passage} = [RFU (test) - RFU (blank)/RFU (equilibrium) - RFU (blank)]*100$$

Permeability Classification:

TABLE 17

| Permeability | Papp (nm/s) |
|---|---|
| Low | <50 |
| Moderate | 50-200 |
| High | >200 |

Efflux ratio = Papp $B$-$A$/Papp $A$-$B$

Efflux ratio ≥ 2 indicates that the drug is a P-gp substrate

Results

Unidirectional Assay (FIG. 1)

TABLE 18

| Drug | Concentration (µM) | Papp (A-B) nm/s |
|---|---|---|
| Caffeine | 10 | 921.89 |
| Atenolol | 50 | 32.77 |
| TDF | 50 | 65.84 |
| (MD1431532) | 100 | 63.54 |
| TAF (VRD-1063/16/187) | 50 | 58.59 |
|  | 100 | 53.89 |

Figure 2:
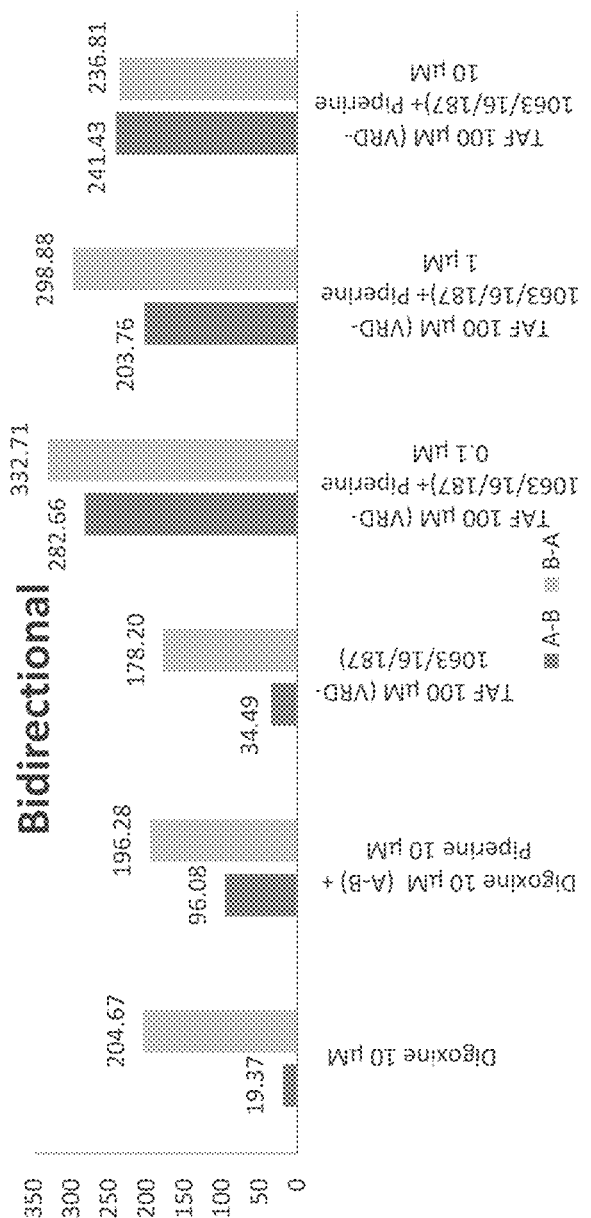
FIG. 2 depicts a bar graph of results from a bidirectional assay of Digoxine 10 µM, Digoxine 10 µM (A-B)+Piperine 10 µM, TAF 100 µM (VRD-1063/16/187), TAF 100 µM (VRD-1063/16/187)+Piperine 0.1 µM and TAF 100 µM (VRD-1063/16/187)+Piperine 10 µM. Results showed that TAF absorption is increased with piperine by decreasing the efflux ratio of TAF.

Bidirectional Assay (FIG. 2)

TABLE 19

| Sample | A-B Papp (nm/s) | B-A Papp (nm/s) | Efflux ratio | % P-gp inhibition |
|---|---|---|---|---|
| Digoxine 10 µM | 19.37 | 204.67 | 10.57 | 0.00 |
| Digoxine 10 µM (A-B) + Piperine 10 µM | 96.08 | 196.28 | 2.04 | 80.67 |
| TAF 100 µM (VRD-1063/16/187) | 34.49 | 178.20 | 5.17 | 0.00 |
| TAF 100 µM (VRD-1063/16/187) + Piperine 0.1 µM | 282.66 | 332.71 | 1.18 | 77.22 |
| TAF 100 µM (VRD-1063/16/187) + Piperine 1 µM | 203.76 | 298.88 | 1.47 | 71.61 |
| TAF 100 µM (VRD-1063/16/187) + Piperine 10 µM | 241.43 | 236.81 | 0.98 | 81.02 |

Conclusions

The TDF and TAF are observed to be low to moderately permeable drugs. Further, TAF absorption is increased with piperine by decreasing the efflux ratio of TAF. The above data indicates that TAF is a substrate of efflux transporter and thus its bioavailability is low. As can be seen in the data, the A-B Papp was 34.49 nm/s and its efflux ratio was 5.17. By adding piperine which is a known inhibitor of efflux transporters, the A-B, Papp increased to more than 282.66 nm/s while the efflux ratio decreased to less than 1.18. Thus indicating addition of piperine improves the permeability. Therefore, it can be concluded that the use of piperine decreases efflux ratio which in turn would increase its bioavailability.

II) Material

Digoxin (known P-gp substrate), Dolutegravir (KK1406229), HBSS buffer, MES hydrate, HEPES powder, Fetal bovine serum (FBS), Minimum essential medium (MEM), Lucifer yellow, Piperine (P-gp inhibitor), Cobicistat (P-gp inhibitor).

Method

1) Caco-2 Cell Culture

Caco-2 cells were cultured in MEM media with 10% serum and seeded at a density of 75000 cells per mL and cultured for 21 days in a 24-well trans-well plate at 37° C., 5% $CO_2$. The monolayer integrity was checked intermittently (Day 0-21) using Trans Epithelial Electric Resistance (TEER). Cells were treated with drugs as follows:

2) Bidirectional Assay (A-B and B-A) to Study the Effect of Piperine (P-Gp Inhibitor) on the Permeability Plate Plan

TABLE 20

|   | 1 | 2 | 3 | 4 | 5 | 6 |
|---|---|---|---|---|---|---|
| A | Digoxine 10 µM (A-B) | Dolutegravir 5 µM A-B | Dolutegravir 5 µM + Piperine 1 µM A-B | Dolutegravir 5 µM + Piperine 10 µM A-B | Dolutegravir 5 µM + Verapamil 1 µM A-B | Dolutegravir 5 µM + Verapamil 10 µM A-B |
| B |   |   |   |   |   |   |
| C | Digoxine 10 µM (B-A) | Dolutegravir 5 µM B-A | Dolutegravir 5 µM + Piperine 1 µM B-A | Dolutegravir 5 µM + Piperine 10 µM B-A | Dolutegravir 5 µM + Verapamil 1 µM B-A | Dolutegravir 5 µM + Verapamil 10 µM B-A |
| D |   |   |   |   |   |   |

Assay Protocol

400 µL samples were added to the wells as per the plate setup to the apical side in duplicates with 800 µL HBSS pH 7.4 in the basal wells. Samples were collected at 60, 90 and 120 minutes from the basal side. Mass balance samples at 0 and 120 minutes were collected from the apical side.

For B-A, 800 µL of the respective dilutions were added to the basal side in duplicates with 400 µL HBSS pH 7.4 in the apical wells. Samples were collected at 60, 90 and 120 minutes from the apical side. Mass balance samples at 0 and 120 minutes were collected from the basal side.

The samples were analyzed on LCMS-MS. At the end of the experiment the monolayer integrity was checked using Lucifer yellow, and calculating the % rejection of Lucifer yellow by incubating cells with 100 µg/mL Lucifer.

3) Data Analysis:

Papp was calculated as follows:

The apparent permeability (Papp) in units per second can be calculated by using the following equation, For single point method:

$$Papp = (V/(T*A))*(C_0/C_t)$$

For multi-point method:

$$Papp = (dQ/dt)/(A*C_0)$$

$$\text{\% Mass balance} = 100 - [C_{R120}*V_R + C_{D120}*V_D/C_0*V_D]$$

For Lucifer yellow,

% Lucifer Yellow Passage=[RFU (test)−RFU (blank)/RFU (equilibrium)−RFU (blank)]*100

Permeability Classification:

TABLE 21

| Permeability | Papp (nm/s) |
|---|---|
| Low | <50 |
| Moderate | 50-200 |
| High | >200 |

Efflux ratio=Papp $B\text{-}A$/Papp $A\text{-}B$

Efflux ratio≥2 indicates that the drug is a P-gp substrate

Results

Figure 3:
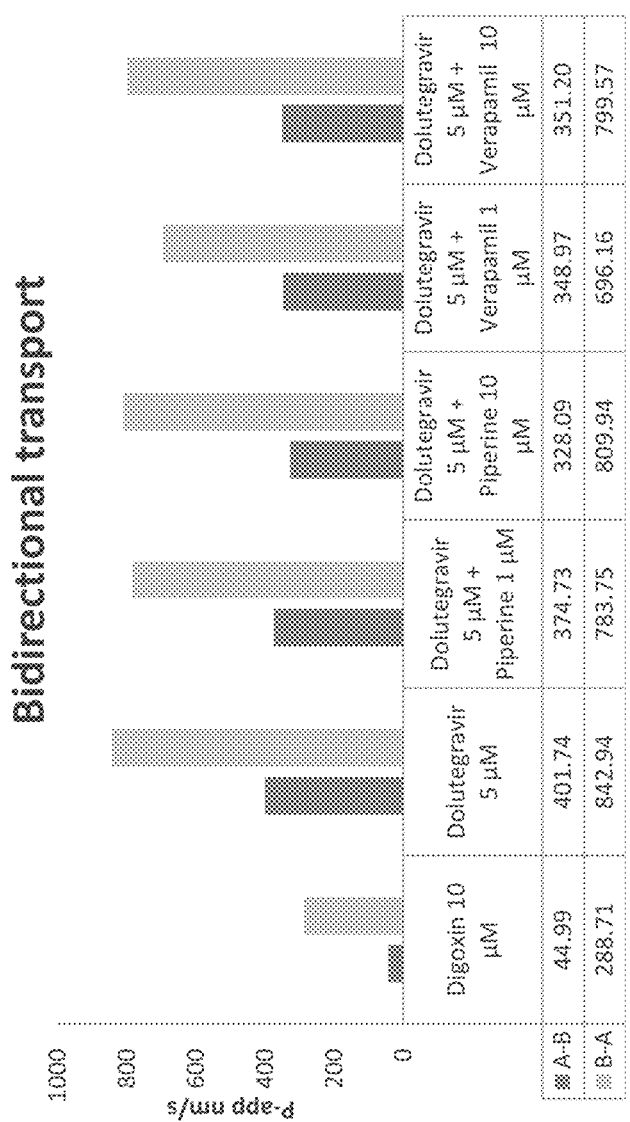
FIG. 3 depicts a bar graph of results from a bidirectional assay of Digoxin 10 µM, Dolutegravir 5 µM, Dolutegravir 5 µM+Piperine 1 µM, Dolutegravir 5 µM+Piperine 10 µM, Dolutegravir 5 µM+Verapamil 1 µM, and Dolutegravir 5 µM+Verapamil 10 µM.

Bidirectional Assay (FIG. 3)

TABLE 22

| Drug | Papp nm/s A-B | Papp nm/s B-A | Efflux ratio |
|---|---|---|---|
| Digoxin 10 µM | 44.99 | 288.71 | 6.41 |
| Dolutegravir 5 µM | 401.74 | 842.94 | 2.09 |
| Dolutegravir 5 µM + Piperine 1 µM | 374.73 | 783.75 | 3.50 |
| Dolutegravir 5 µM + Piperine 10 µM | 328.09 | 809.94 | 2.46 |
| Dolutegravir 5 µM + Verapamil 1 µM | 348.97 | 696.16 | 1.99 |
| Dolutegravir 5 µM + Verapamil 10 µM | 351.20 | 799.57 | 2.27 |

Conclusions

Dolutegravir is a known P-gp substrate. Dolutegravir is a high permeable drug and piperine does not affect the permeability of dolutegravir across the caco-2 monolayer. Therefore, it can be concluded that the use of piperine decreases efflux ratio which in turn would increase its bioavailability.

III) Material

Digoxin (known P-gp substrate), Darunavir (DN0011215), HBSS buffer, MES hydrate, HEPES powder, Fetal bovine serum (FBS), Minimum essential medium (MEM), Lucifer yellow, Piperine (P-gp inhibitor), Cobicistat (P-gp inhibitor)

Method

1.) Caco-2 Cell Culture

Caco-2 cells were cultured in MEM media with 10% serum and seeded at a density of 75000 cells per mL and cultured for 21 days in a 24-well trans-well plate at 37° C., 5% $CO_2$. The monolayer integrity was checked intermittently (Day 0-21) using Trans Epithelial Electric Resistance (TEER). Cells were treated with drugs as follows:

2.) Bidirectional Assay (A-B and B-A) to Study the Effect of Piperine (P-Gp Inhibitor) on the Permeability Plate Plan

TABLE 23

|   | 1 | 2 | 3 | 4 | 5 | 6 |
|---|---|---|---|---|---|---|
| A | Digoxine 10 µM (A-B) | Darunavir 40 µM A-B | Darunavir 40 µM + Piperine 1 µM A-B | Darunavir 40 µM + Piperine 10 µM A-B | Darunavir 40 µM + Cobicistat 10 µM A-B | Darunavir 40 µM + Cobicistat 100 µM A-B |
| B |   |   |   |   |   |   |
| C | Digoxine 10 µM (B-A) | Darunavir 40 µM B-A | Darunavir 40 µM + Piperine 1 µM B-A | Darunavir 40 µM + Piperine 10 µM B-A | Darunavir 40 µM + Cobicistat 10 µM B-A | Darunavir 40 µM + Cobicistat 100 µM B-A |
| D |   |   |   |   |   |   |

Assay Protocol

400 µL samples were added to the wells as per the plate setup to the apical side in duplicates with 800 µL HBSS pH 7.4 in the basal wells. Samples were collected at 60, 90 and 120 minutes from the basal side. Mass balance samples at 0 and 120 minutes were collected from the apical side.

For B-A, 800 µL of the respective dilutions were added to the basal side in duplicates with 400 µL HBSS pH 7.4 in the apical wells. Samples were collected at 60, 90 and 120 minutes from the apical side. Mass balance samples at 0 and 120 minutes were collected from the basal side.

The sample were analyzed on LCMS-MS. At the end of the experiment, the monolayer integrity was checked using and Lucifer yellow, calculating the % rejection of Lucifer yellow by incubating cells with 100 µg/mL Lucifer.

3.) Data Analysis:

Papp was calculated as follows:
The apparent permeability (Papp) in units per second can be calculated by using the following equation,
For single point method:

$$Papp=(V/(T*A))*(C0/Ct)$$

For multi-point method:

$$Papp=(dQ/dt)/(A*C0)$$

$$Mass\ balance=100-[CR120*VR+CD120*VD/C0*VD]$$

For Lucifer yellow, $$\%\ Lucifer\ Yellow\ Passage=[RFU\ (test)-RFU\ (blank)/RFU\ (equilibrium)-RFU\ (blank)]*100$$

Permeability Classification:

TABLE 24

| Permeability | Papp (nm/s) |
|---|---|
| Low | <50 |
| Moderate | 50-200 |
| High | >200 |

Efflux ratio=Papp B-A/Papp A-B

Efflux ratio≥2 indicates that the drug is a P-gp substrate

Results

Figure 4:
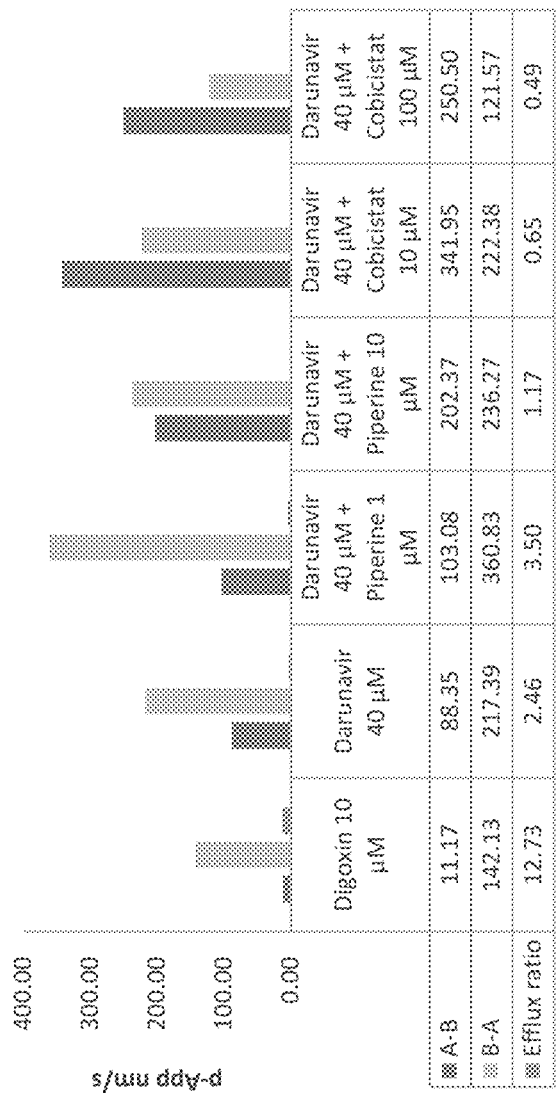
FIG. 4 depicts a bar graph of results from a bidirectional assay of Digoxin 10 µM, Darunavir 40 µM, Darunavir 40 µM+Piperine 1 µM, Darunavir 40 µM+Piperine 10 µM, Darunavir 40 µM+Cobicistat 10 µM, and Darunavir 40 µM+Cobicistat 100 µM. Results showed that absorption of Darunavir is increased with piperine by decreasing the efflux ratio of TAF.

Bidirectional Assay (FIG. 4)

TABLE 25

| Drug | Papp nm/s | | Efflux ratio |
|---|---|---|---|
|   | A-B | B-A |   |
| Digoxin 10 µM | 11.17 | 142.13 | 12.73 |
| Darunavir 40 µM | 88.35 | 217.39 | 2.46 |
| Darunavir 40 µM + Piperine 1 µM | 103.08 | 360.83 | 3.50 |
| Darunavir 40 µM + Piperine 10 µM | 202.37 | 236.27 | 1.17 |
| Darunavir 40 µM + Cobicistat 10 µM | 341.95 | 222.38 | 0.65 |
| Darunavir 40 µM + Cobicistat 100 µM | 250.50 | 121.57 | 0.49 |

Conclusions

Darunavir is a known P-gp substrate. Absorption of Darunavir is increased with piperine by decreasing the efflux ratio of TAF. Therefore, it can be concluded that the use of piperine decreases efflux ratio which in turn would increase its bioavailability.

IV) Material

Digoxin (known P-gp substrate), TDF, HBSS buffer, MES hydrate, HEPES powder, Fetal bovine serum (FBS), Minimum essential medium (MEM), Lucifer yellow, Piperine (P-gp inhibitor), Cobicistat (P-gp inhibitor), Tetrahydropiperine (P-gp inhibitor)

Method

1.) Caco-2 Cell Culture

Caco-2 cells were cultured in MEM media with 10% serum and seeded at a density of 75000 cells per mL and cultured for 21 days in a 24-well trans-well plate at 37° C., 5% $CO_2$. The monolayer integrity was checked intermittently (Day 0-21) using Trans Epithelial Electric Resistance (TEER). Cells were treated with drugs as follows:

2.) Bidirectional Assay (A-B and B-A) to Study the Effect of Piperine (P-Gp Inhibitor) and Tetrahydropiperine on the Permeability Plate Plan

TABLE 26

|   | 1 | 2 | 3 | 4 | 5 |
|---|---|---|---|---|---|
| A | Digoxine 10 µM (A-B) | TDF 200 µM (A-B) | TDF 100 µM (A-B) | TDF 100 µM (A-B) + Piperine 10 µM | TDF 100 µM (A-B) + THpiperine 10 µM |
| C | Digoxine 10 µM (B-A) | TDF 200 µM (B-A) | TDF 100 µM (B-A) | TDF 100 µM (B-A) + Piperine 10 µM | TDF 100 µM (B-A) + Thpiperine 10 µM |

Assay Protocol

400 µL samples were added to the wells as per the plate setup to the apical side in duplicates with 800 µL HBSS pH 7.4 in the basal wells. Samples were collected at 60, 90 and 120 minutes from the basal side. Mass balance samples at 0 and 120 minutes were collected from the apical side.

For B-A, 800 µL of the respective dilutions were added to the basal side in duplicates with 400 µL HBSS pH 7.4 in the apical wells. Samples were collected at 60, 90 and 120 minutes from the apical side. Mass balance samples at 0 and 120 minutes were collected from the basal side.

The sample were analyzed on LCMS-MS. At the end of the experiment the monolayer integrity was checked using and Lucifer yellow, calculating the % rejection of Lucifer yellow by incubating cells with 100 µg/mL Lucifer.

3.) Data Analysis:

Papp was calculated as follows:
The apparent permeability (Papp) in units per second can be calculated by using the following equation,
For single point method:

Papp=(V/(T*A))*(C0/Ct)

For multi-point method:

Papp=(dQ/dt)/(A*C0)

% Mass balance=100−[CR120*VR+CD120*VD/C0*VD]

For Lucifer yellow, % Lucifer Yellow Passage=[RFU (test)−RFU (blank)/RFU (equilibrium)−RFU (blank)]*100

Permeability Classification:

TABLE 27

| Permeability | Papp (nm/s) |
|---|---|
| Low | <50 |
| Moderate | 50-200 |
| High | >200 |

Efflux ratio=Papp B-A/Papp A-B

Efflux ratio≥2 indicates that the drug is a P-gp substrate

Results

Figure 5:
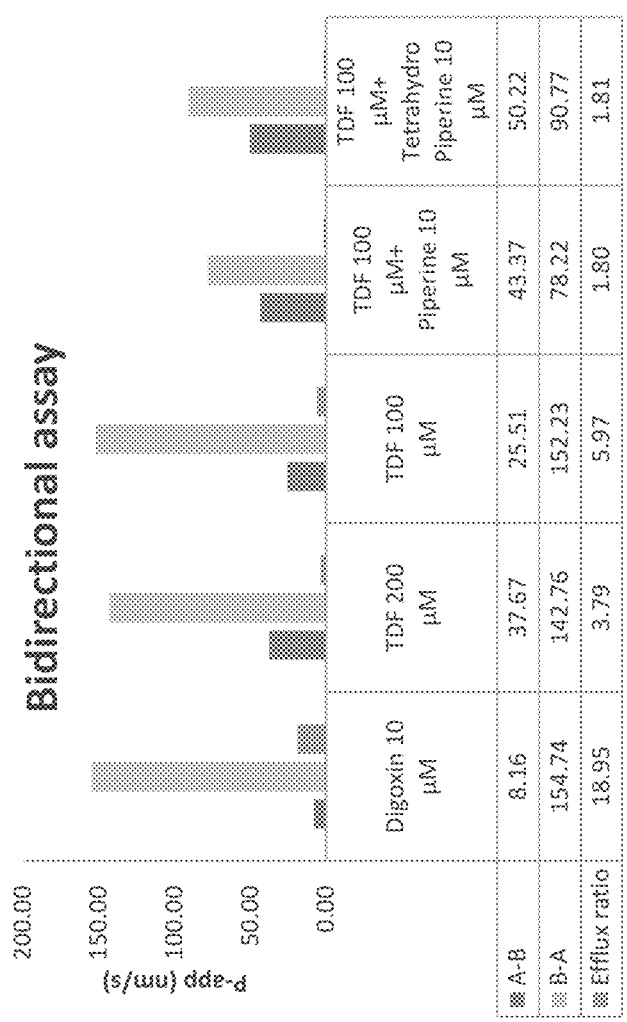
FIG. 5 depicts a bar graph of results from a bidirectional assay of Digoxin 10 μM TDF 200 μM, TDF 100 μM, TDF 100 μM+Piperine 10 μM, and TDF 100 μM+Tetrahydro Piperine 10 μM. Results showed that absorption of TDF is increased with piperine by decreasing the efflux ratio, absorption of TDF is increased with tetrahydropiperine by decreasing the efflux ratio, and comparable improvement in permeability of TDF was seen by both Piperine and tetrahydropiperine.

Bidirectional Assay (FIG. 5)

TABLE 28

| Drug | Papp nm/s A-B | Papp nm/s B-A | Efflux ratio |
|---|---|---|---|
| Digoxin 10 µM | 8.16 | 154.74 | 18.95 |
| TDF 200 µM | 37.67 | 142.76 | 3.79 |
| TDF 100 µM | 25.51 | 152.23 | 5.97 |
| TDF 100 µM + Piperine 10 µM | 43.37 | 78.22 | 1.80 |
| TDF 100 µM + Tetrahydro Piperine 10 µM | 50.22 | 90.77 | 1.81 |

Conclusions

TDF is a known P-gp substrate. Absorption of TDF is increased with piperine by decreasing the efflux ratio. Further, absorption of TDF is increased with tetrahydropiperine by decreasing the efflux ratio. Comparable improvement in permeability of TDF was seen by both Piperine and tetrahydropiperine. Therefore, it can be concluded that the use of piperine and tetrahydropiperine decreases efflux ratio which in turn would increase its bioavailability.

Animal Study

In Vivo Rat PK Study

The objective of this non-GLP study was to determine the pharmacokinetics of the TDF alone and in combinations with piperine in different groups of male Wistar rats after single dose intravenous administration and oral administration. This study was performed with approval from the Institutional Animal Ethics Committee (IAEC) in accordance with the requirement of Committee for the Purpose of Control and Supervision of Experiments on Animals (CPCSEA), India.

Study Design

The study was conducted using six male Wistar rats in each group as shown in Table 30 below.

TABLE 29

| Group | Test compound | Formulation vehicle | Route | Dose mg/kg | Dose vol mL/kg | Concentration (mg/mL) |
|---|---|---|---|---|---|---|
| 1 | TDF | Normal saline | IV | 7.75 | 5 | 1.55 |
| 2 | TDF | 0.5% Sodium Carboxy Methyl Cellulose in double distilled (DS) water | PO | 31 | 5 | 6.2 |
| 3 | TDF | 0.5% Sodium Carboxy Methyl Cellulose in DS water | PO | 15.5 | 5 | 3.1 |
| 4 | TDF + Piperine | 0.5% Sodium Carboxy Methyl Cellulose in DS water | PO | 31 + 2 | 5 | 6.2 + 0.4 |
| 5 | TDF + Piperine | 0.5% Sodium Carboxy Methyl Cellulose in DS water | PO | 15.5 + 2 | 5 | 3.1 + 0.4 |

Formulation Preparation

The solution formulations were prepared as follows:

Intravenous Route:

Required quantity of Compound B (TDF) (23.03 mg) was weighed and to this 10.94 mL of vehicle (Normal saline) was added, vortexed and sonicated for 2 minutes to make a clear formulation.

Per Oral Route:

For Group 2: Required quantity of Compound B (79.37 mg) was weighed and to this 9.42 mL of vehicle (Na Carboxy Methylcellulose) was added, vortexed and sonicated for 2 minutes to make formulation of 6.2 mg/mL concentration.

For Group 3: Required quantity of Compound B (46.14 mg) was weighed and to this 10.95 mL of vehicle (Na Carboxy Methylcellulose) added, vortexed and sonicated for 2 minutes to make a uniform formulation.

For Group 4: Required quantity of Compound B (79.56 mg) was weighed and to this 4.72 mL of vehicle (Na Carboxy Methylcellulose) was added, vortexed and sonicated for 2 minutes to make a clear formulation. Required quantity of Compound B1 (piperine) (18.95 mg) was weighed and to this 22.71 mL of vehicle (Na Carboxy Methylcellulose) was added, vortexed and sonicated for 2 minutes to make a clear formulation. An equal volume (4.72 mL) of each formulation was mixed in separate vials to get 5 mL/kg.

For Group 5: Required quantity of Compound B (47.20 mg) and Compound B1 (18.95 mg) were weighed and to this 5.61 mL of vehicle (Na Carboxy Methylcellulose) was added, vortexed and sonicated for 2 minutes to make a clear formulation. An equal volume (5.61 mL) of each formulation was mixed in separate vials to get 5 mL/kg.

Bioanalysis

Bioanalysis was performed using fit-for-purpose LC-MS/MS method for the quantification of TDF and PMPA in rat plasma samples. The calibration curve (CC) for the method consisted of nine non-zero calibration standards along with a double blank and zero standard samples.

Pharmacokinetic Analysis

Plasma pharmacokinetic parameters were calculated using the non-compartmental analysis tool of Phoenix software (Version 6.3) and were determined from individual animals in each group. The peak plasma concentration (Cmax), time to achieve peak plasma concentration (Tmax), the area under the plasma concentration-time curve (AUC0-t and AUCinf), AUC Extra (%), elimination half-life (T½), clearance (CL), volume of distribution Vd (L/kg) and Mean residence time (MRT) were calculated from the intravenous group. The peak plasma concentration (Cmax), time to achieve peak plasma concentration (Tmax), AUC0-t and AUCinf, AUC Extra (%), Mean residence time (MRT) and absolute oral bioavailability (F) were calculated from the oral group.

Results

The plasma concentration-time data and plasma pharmacokinetic parameters of PMPA following intravenous and oral administration of TDF in male Wistar rats are presented in the Table 31.

TABLE 30

| Route/Dose (mg/kg) | $T_{max}$ (h) | $C_{max}$ (ng/mL) | $AUC_{0-t}$ (h * ng/mL) | $AUC_{0-inf}$ (h * ng/mL) | F (%) |
| --- | --- | --- | --- | --- | --- |
| IV (7.75) G1 | 0.08 ± 0.00 | 2425.44 ± 677.91 | 900.66 ± 213.26 | 1023.37 ± 217.13 | NA |
| PO (31) G2 | 0.71 ± 0.33 | 294.14 ± 140.55 | 1284.52 ± 392.13 | 1407.62 ± 402.73 | 34.39 ± 6.07 |
| PO (15.5) G3 | 0.71 ± 0.70 | 283.43 ± 108.44 | 846.94 ± 128.87 | 904.96 ± 111.76 | 44.22 ± 1.91 |
| PO (B = 31 + B1 = 2) G4 | 0.58 ± 0.20 | 462.52 ± 68.80 | 1487.98 ± 174.80 | 1586.43 ± 164.81 | 38.76 ± 4.82 |
| PO (B = 15.5 + B1 = 2) G5 | 0.50 ± 0.00 | 340.07 ± 118.97 | 955.15 ± 250.07 | 1074.19 ± 307.58 | 52.48 ± 13.48 |

Figure 6:
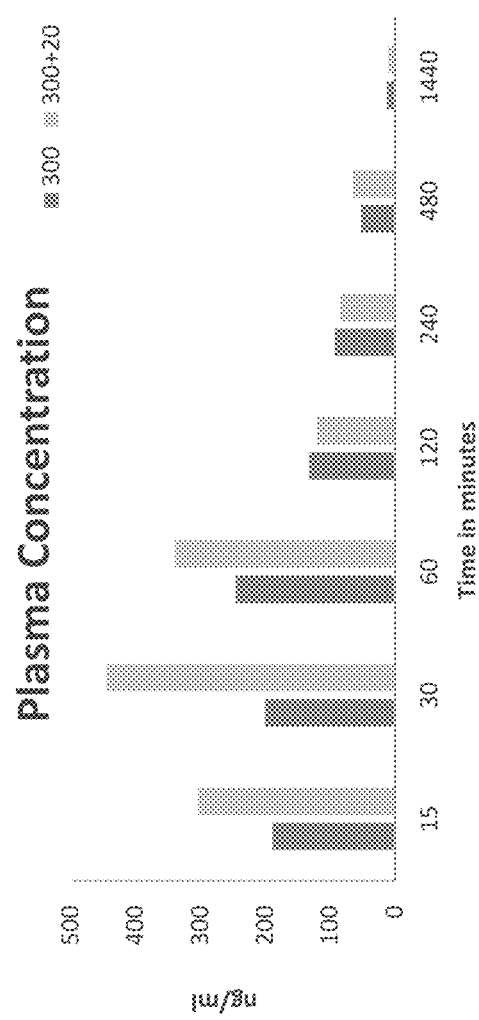
FIG. 6 depicts a bar graph of plasma concentrations of tenofovir for TDF 300 mg and TDF 300 mg+Piperine 20 mg at different time points.
Figure 7:
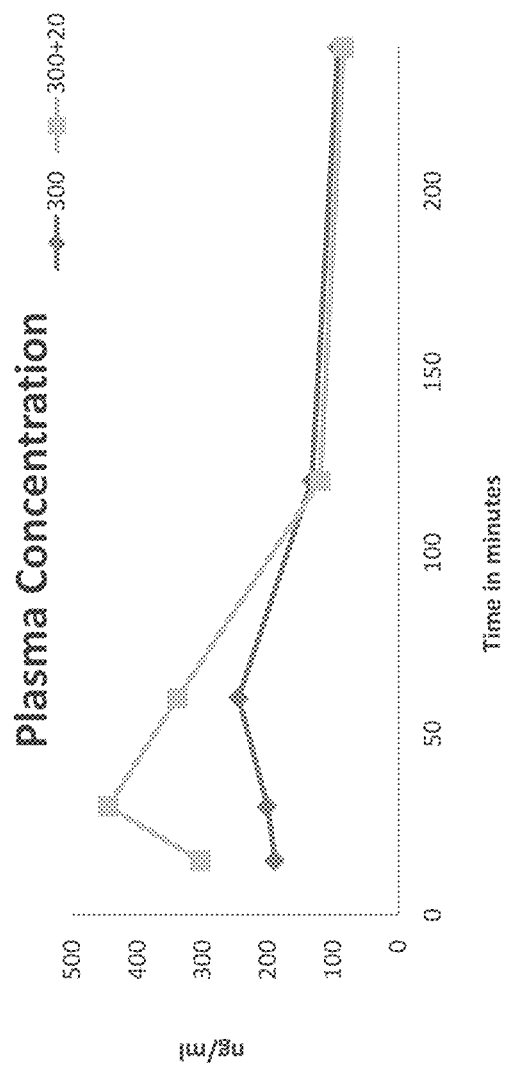
FIG. 7 depicts a bar graph of plasma concentrations of tenofovir for TDF 300 mg and TDF 300 mg+Piperine 20 mg at different time points.

FIGS. 6 and 7 show Plasma concentration of tenofovir for TDF 300 mg and TDF 300 mg+Piperine 20 mg at different time points.

TABLE 31

Cmax, Tmax and AUC values of different combinations

| | 300 mg TDF | 300 mg TDF + 20 mg Piperine | 150 mg TDF | 150 mg TDF + 20 mg Piperine |
| --- | --- | --- | --- | --- |
| Cmax (nM) | 462.26 | 727.23 | 444.96 | 534.59 |
| Tmax (h) | 0.71 | 0.58 | 0.71 | 0.5 |
| AUC | 1407.62 | 1586.53 | 904.96 | 1074.19 |

Figure 8:
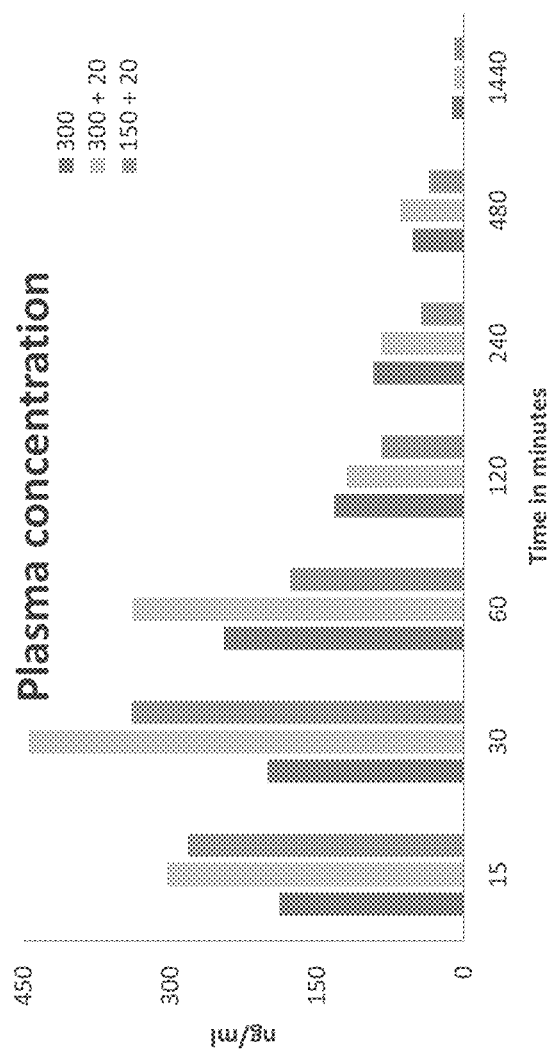
FIG. 8 depicts time dependent plasma concentrations of tenofovir for 300 mg TDF, 300 mg TDF+20 mg piperine and 150 mg TDF+20 mg piperine.

FIG. 8 shows time dependent plasma concentration of tenofovir for 300 mg TDF, 300 mg TDF+20 mg piperine and 150 mg TDF+20 mg piperine Conclusions The rat PK study clearly indicates that the peak plasma concentration of tenofovir significantly increased when TDF is administered in combination with piperine. The results demonstrate a significant bioavailability enhancement when TDF at 150 mg is administered with 20 mg piperine (52.48±13.48) as compared to TDF 300 mg alone (34.39±6.07).

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

All patent and non-patent publications cited in this disclosure are incorporated herein in to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An oral or injectable pharmaceutical composition comprising a therapeutically effective amount of an anti-retroviral drug comprising tenofovir or its pharmaceutically acceptable salts in an amount from about 1 mg to about 300 mg and a therapeutically effective amount of a pharmacokinetic booster or enhancer or derivative thereof comprising tetrahydropiperine in an amount from about 0.5 mg to about 400 mg, the ratio of the anti-retroviral drug to the pharmacokinetic booster or enhancer or derivative thereof is from about 100:1 to about 1:1 by weight, and the pharmacokinetic booster or enhancer or derivative thereof increases the bioavailability of the anti-retroviral drug from about 10% to about 70%.

2. An oral or injectable pharmaceutical composition consisting of a therapeutically effective amount of tenofovir or its pharmaceutically acceptable salts in an amount from about 1 mg to about 300 mg and a therapeutically effective amount of tetrahydropiperine, in an amount from about 0.5 mg to about 400 mg, the ratio of tenofovir to tetrahydropiperine is from about 100:1 to about 1:1 by weight, and increases the bioavailability of the oral or injectable pharmaceutical composition from about 10% to about 70%.

3. The oral or injectable pharmaceutical composition of claim 1, wherein the pharmacokinetic booster or enhancer or derivative thereof reduces a dosing frequency of the anti-retroviral drug that is administered to a patient.

4. An oral or injectable pharmaceutical composition comprising a therapeutically effective amount of an anti-retroviral drug comprising tenofovir or its pharmaceutically acceptable salts in an amount from about 1 mg to about 300 mg; a therapeutically effective amount of a pharmacokinetic booster or enhancer or derivative thereof comprising tetrahydropiperine in an amount from about 0.5 mg to about 400 mg; and one or more pharmaceutically acceptable excipients comprising carriers, diluents, fillers, binders, lubricants, glidants, disintegrants, bulking agents, flavorants or any combination thereof.

5. The oral or injectable pharmaceutical composition of claim 4, wherein the oral composition is in the form of a tablet, mini-tablet, granules, sprinkles, capsules, sachets, powders, pellets, and the injectable composition is in the form of a solution, suspension, emulsion, lyophilized powder or in the form of a kit.

6. The oral or injectable pharmaceutical composition of claim 4, wherein the oral or injectable pharmaceutical composition is for use in the treatment or prophylaxis of diseases caused by retroviruses.

7. The oral or injectable pharmaceutical composition of claim 4, wherein the oral or injectable pharmaceutical composition is for use in the treatment of diseases caused by hepatitis B viruses.

8. A method of treating diseases caused by retroviruses or hepatitis B viruses in a patient in need of such treatment, the method comprising: administering a pharmaceutical composition comprising (i) a therapeutically effective amount of an anti-retroviral drug or an antiviral drug comprising tenofovir or its pharmaceutically acceptable salts in an amount from about 1 mg to about 300 mg; (ii) a therapeutically effective amount of a pharmacokinetic booster or enhancer or derivative thereof comprising tetrahydropiperine in an amount from about 0.5 mg to about 400 mg; and (iii) one or more pharmaceutically acceptable excipients comprising carriers, diluents, fillers, binders, lubricants, glidants, disintegrants, bulking agents, flavorants or any combination thereof.

9. The method according to claim 8, wherein the diseases caused by retroviruses comprises acquired immune deficiency syndrome or an HIV infection.

10. A method of making a pharmaceutical composition that enhances the bioavailability of an anti-retroviral drug, the method comprising: mixing a therapeutically effective amount of an anti-retroviral drug comprising tenofovir or its pharmaceutically acceptable salts in an amount from about 1 mg to about 300 mg and a therapeutically effective amount of a pharmacokinetic booster or enhancer or derivative thereof comprising tetrahydropiperine in an amount from about 0.5 mg to about 400 mg with one or more pharmaceutically acceptable excipients to make the pharmaceutical composition.

11. A kit for treating disease caused by retroviruses or hepatitis B viruses, the kit comprising a therapeutically effective amount of at least one anti-retroviral drug comprising tenofovir or its pharmaceutically acceptable salts in an amount from about 1 mg to about 300 mg and a therapeutically effective amount of at least one pharmacokinetic booster or enhancer or derivative thereof comprising tetrahydropiperine in an amount from about 0.5 mg to about 400 mg, wherein the at least one anti-retroviral drug is in a separate composition from the at least one pharmacokinetic booster or enhancer or derivative thereof.

12. A method of enhancing the bioavailability of an oral anti-retroviral drug, the method comprising: providing a therapeutically effective amount of at least one anti-retroviral drug comprising tenofovir or its pharmaceutically acceptable salts in an amount from about 1 mg to about 300 mg and providing a therapeutically effective amount of at least one pharmacokinetic booster or enhancer or derivative thereof comprising tetrahydropiperine in an amount from about 0.5 mg to about 400 mg.

13. The oral or injectable composition of claim 1, wherein the pharmaceutically acceptable salt of tenofovir is tenofovir alfenamide fumarate or tenofovir disoproxil fumarate.

14. The oral or injectable composition of claim 13, wherein absorption of tenofovir disoproxil fumarate (TDF) is increased with tetrahydropiperine by decreasing the efflux ratio to 1.81.

* * * * *